United States Patent
Tusman et al.

(10) Patent No.: US 10,595,729 B2
(45) Date of Patent: Mar. 24, 2020

(54) METHOD AND APPARATUS FOR PREDICTION OF FLUID RESPONSIVENESS IN MECHANICALLY VENTILATED SUBJECTS

(71) Applicant: MAQUET CRITICAL CARE AB, Solna (SE)

(72) Inventors: Gerardo Tusman, Buenos Aires (AR); Stephan Boehm, Elbe (DE); Fernando Suarez Sipman, Madrid (ES); Magnus Hallback, Danderyd (SE)

(73) Assignee: Maquet Critical Care AB, Solna (SE)

( * ) Notice: Subject to any disclaimer, the term of this patent is extended or adjusted under 35 U.S.C. 154(b) by 304 days.

(21) Appl. No.: 15/505,814

(22) PCT Filed: Aug. 26, 2015

(86) PCT No.: PCT/SE2015/050903
§ 371 (c)(1),
(2) Date: Feb. 22, 2017

(87) PCT Pub. No.: WO2016/032391
PCT Pub. Date: Mar. 3, 2016

(65) Prior Publication Data
US 2017/0273573 A1    Sep. 28, 2017

(30) Foreign Application Priority Data
Aug. 27, 2014    (WO) .................. PCT/SE2014/050976

(51) Int. Cl.
*A61B 5/02*    (2006.01)
*A61B 5/091*    (2006.01)
(Continued)

(52) U.S. Cl.
CPC .......... *A61B 5/02028* (2013.01); *A61B 5/083* (2013.01); *A61B 5/0836* (2013.01);
(Continued)

(58) Field of Classification Search
CPC ..... A61B 5/02028; A61B 5/083; A61B 5/091; A61B 5/0836; A61M 16/026; A61M 2016/0042; A61M 2230/432
See application file for complete search history.

(56) References Cited

FOREIGN PATENT DOCUMENTS

| EP | 2301613 A1 | 3/2011 |
|---|---|---|
| EP | 2641536 A1 | 9/2013 |

OTHER PUBLICATIONS

Young et al: "Changes in End-Tidal Carbon Dioxide and Volumetric Carbon Dioxide as Predictors of Volume Responsiveness in Hemodynamically Unstable Patients", Journal of Cardiothoracic and Vascular Anesthesia, vol. 27, No. 4, 1 pp. 681-684 (2013).
(Continued)

*Primary Examiner* — Bradley J Osinski
(74) *Attorney, Agent, or Firm* — Schiff Hardin LLP

(57) ABSTRACT

In a method and breathing apparatus for prediction of fluid responsiveness of a subject connected to a breathing apparatus, at least one parameter is monitored that is indicative of a degree of carbon dioxide elimination of the subject, and a positive end expiratory pressure PEEP regulator of the breathing apparatus is operated to apply a PEEP maneuver in which a PEEP applied to the subject is changed from a first PEEP level to a second PEEP level. A processor predicts the fluid responsiveness of the subject based on a change in the monitored parameter, following the change in PEEP.

25 Claims, 3 Drawing Sheets

(51) Int. Cl.
*A61B 5/083* (2006.01)
*A61M 16/00* (2006.01)

(52) U.S. Cl.
CPC ......... *A61B 5/091* (2013.01); *A61M 16/0051* (2013.01); *A61M 16/026* (2017.08); *A61M 2016/0042* (2013.01); *A61M 2230/432* (2013.01)

(56) References Cited

OTHER PUBLICATIONS

Babik et al: "Effects of Respiratory Mechanics on the Capnogram Phases: Importance of Dynamic Compliance of the Respiratory System", Critical Care, vol. 16, No. 5, p. R177, (10 pages) (2012).
Peyton, "Continuous Minimally Invasive Pen-Operative Monitoring of Cardiac Output by Pulmonary Capnotracking: Comparison With Thermodilution and Transesophageal Echocardiography", Journal of Clinical Monitoring and Computing, vol. 26, No. 2, pp. 121-132 (2012).

METHOD AND APPARATUS FOR PREDICTION OF FLUID RESPONSIVENESS IN MECHANICALLY VENTILATED SUBJECTS

BACKGROUND OF THE INVENTION

Field of the Invention

The present invention relates to a method, a breathing apparatus and a computer program for prediction of fluid responsiveness of a subject undergoing mechanical ventilation.

Description of the Prior Art

Hemodynamic monitoring—i.e. the continuous display and recording of hemodynamic parameters to inform about the status of the cardiovascular system by means of specific devices—is a cornerstone in the care of critically ill patients. The main goal of hemodynamic monitoring is to assess the function of the cardiovascular system in order to diagnose and guide the treatment of any dangerous acute cardiovascular event. There is a general consensus among clinicians that organ function is preserved by maintaining a normal cardiovascular status in which oxygen delivery to the tissues largely matches their oxygen consumption. Cardiovascular instability compromises peripheral oxygen delivery and, if remained undetected or inappropriately treated, can affect normal tissue function and lead to organ failure. Hemodynamic monitoring is especially successful when it helps detecting any hemodynamic instability before organ dysfunction ensues and to monitor the magnitude and time of proactive therapeutic interventions aimed at preventing it. Thus, hemodynamic monitoring must be regarded as an essential component in the initial and continued management of all critically ill patients treated in the emergency, operating room and in the intensive care unit. Once organ dysfunction has ensued, hemodynamic monitoring and treatment alone are of little help in improving patient's outcome (Vincent J-L, Rhodes A, Perel A, Martin G S, Rocca Della G, Vallet B, Pinsky M R, Hofer C K, Teboul J-L, de Boode W-P, et al.: Clinical review: Update on hemodynamic monitoring—a consensus of 16. Crit Care 2011, 15:229, Rivers E, et al. Early goal-directed therapy in the treatment of severe sepsis and septic shock. N Engl Med J 2001; 345: 1368-1377, Bland R D, et al. Hemodynamic and oxygen transport patterns in surviving and non-surviving postoperative patients. Crit Care Med 1985; 13: 85-90, Connors A F, et al. The effectiveness of right heart catheterization in the initial care of critically ill patients. JAMA 1996; 276: 889-897).

One of the most important determinants of the status of the cardiovascular system is its effective volume of blood, or its volemia. There is a certain amount of blood within such system in a healthy state, called normovolemia or euvolemia, which is related to normal cardiovascular function and hence to an adequate delivery of oxygenated blood to all body tissues. In contrast, any decrease in intravascular volume or hypovolemia due to for example bleeding, dehydration, microcirculatory failure, third space fluid sequestration or excessive vasodilation may cause a deficit in oxygen delivery to tissues and if severe and/or prolonged enough may lead to organ failure. A concept inherent to volemia is preload. Preload is defined as the volume of blood within the ventricles at the end of diastole that stretch the myocardial fibers to a certain sarcomere length necessary for a normal effective and efficient heart muscle contraction during systole. Any decrease in cardiac preload will result in a decrease of the heart's efficiency and in systemic hypoperfusion of different degrees, which can frequently coexist with normal standard hemodynamic parameters such as mean arterial or central venous pressure.

Standard hemodynamic monitoring systems can easily detect severe hypovolemic states but often fail in diagnosing moderate to mild hypovolemia. This is an important limitation in the monitoring of critical care patients because when such occult hypovolemia remains for many hours it can be associated with several complications such as acute renal failure, heart ischemia, cerebral stroke or wound infection among others. This occult hypovolemia is manifested as a "preload dependency" which in medical terms means that the cardiovascular system operates at the steep portion of the Frank-Starling relationship, illustrated in FIG. 1. According to this relationship the ventricle will respond with an increase in cardiac output (more often expressed as stroke volume SV or the volume ejected by the ventricle with each systole) in response to the administration of intravascular volume. In other words the patient is "fluid responsive".

With reference to FIG. 1, the Frank-Starling relationship describes the relation between volemia (preload) and cardiac output (CO) or stroke volume (SV). In the volume responsive part, denoted by reference numeral (a), an increase in volemia will cause a corresponding increase in stroke volume. In a normovolemic patient the same increment in volume will only cause a very modest increase or no increase at all in SV, as illustrated by the scenario denoted by reference numeral (b). In a volume overloaded state (flat portion of the Frank-Starling relationship) any given volume will not affect SV but may lead to fluid overload of lungs and body.

An important distinction to be made here is that being fluid responsive does not necessarily mean that the patient is hypovolemic as fluid responsiveness is a normal physiological status due to the high capacitance of the venous system. It only tells us that the cardiovascular system will respond with a certain increase in CO to the administration of intravenous fluids.

Intravenous fluid administration is considered the first line intervention in hemodynamically unstable patients to restore euvolemia (or in other words, to optimize preload). There is established evidence that optimizing high-risk surgical patients by volume loading improves hemodynamics and decreases the incidence of postoperative complications and hospital mortality (Kim I B, Bellomo R, Fealy N, et al. A pilot study of the epidemiology and association of pulse pressure variation in cardiac surgery patients. Crit Care Resusc 2011; 13: 17-23, Gan T J, Soppitt A, Maroof M, et al. Goal-directed intraoperative fluid administration reduces length of hospital stay after major surgery. Anesthesiology 2002; 97: 820-6, Lopes M R, Oliveira M A, Lemos I P, et al. Goal-directed fluid management based on pulse pressure variation monitoring during high-risk surgery: a pilot randomized controlled trial. Crit Care 2007; 11: R100). However, only 50% of hemodynamically unstable patients are fluid responsive and it has been clearly established that an excess of intravenous fluids (i.e. over-resuscitation) is associated with an increased morbi-mortality as it can precipitate lung edema, worsen cor pulmonale or induce left heart failure, as discussed e.g. in Bellamy M C: Wet, dry or something else? British Journal of Anaesthesia 2006, 97:755-757 of the appended list of references.

Therefore, the routine assessment of fluid responsiveness (i.e. the prospective identification of patients in whom intravenous administration of fluids will improve hemodynamics) is becoming an essential component of goal-directed fluid therapy protocols aimed at both, optimizing the intravascular volume status and avoiding the deleterious consequences of fluid overload (Salzwedel C, Puig J, Carstens A, Bein B, Molnar Z, Kiss K, Hussain A, Belda J, Kirov M Y, Sakka S G, Reuter D A. Perioperative goal-directed hemodynamic therapy based on radial arterial pulse pressure variation and continuous cardiac index trending reduces postoperative complications after major abdominal surgery: a multi-center, prospective, randomized study. Crit Care 2013; 17: R191, Brandstrup B, Tonnesen H, Beier-Holgersen R, et al. Effects of intravenous fluid restriction on postoperative pulmonary complications: comparison of two perioperative fluid regiments: a randomized assessor-blinded multicenter trial Ann Surg 2003; 238: 641-8).

State of the Art Techniques for Fluid Responsiveness Assessment

The correct assessment of the effective intravascular volemia and state of fluid responsiveness remains one of the major challenges for ICU physicians and anesthesiologists dealing with hemodynamically unstable patients. Decisions on type, amount and timing of fluid therapy are however of great clinical relevance as both hypovolemia and hypervolemia are associated with increased morbidity and mortality. There are however no such things as gold standard parameters and preload remains difficult to assess at the bedside.

To determine the cardiovascular status and the state of fluid responsiveness of a patient with an acceptable degree of accuracy clinicians must assess the dynamic response of available hemodynamic variables to a defined intervention that creates a perturbation of sufficient magnitude. This is one of the core principles behind the concept of functional hemodynamic monitoring which is the pluripotential approach to interpolation of physiological data using a proactive intervention to identify clinical parameters with robust sensitivity and specificity to identify cardiovascular instability and volume responsiveness (Pinsky M R. Functional hemodynamic monitoring. Intensive Care Med 2002; 28: 386-8). The two most well established interventions are the fluid challenge and the passive leg raising (PLR) maneuver. During a fluid challenge a specified amount of volume is infused intravenously over a short period of time. A PLR is a preload redistribution maneuver (i.e. a kind of autotransfusion) during which the legs of a patient lying in the supine position are raised 45° over the horizontal plane while the trunk is maintained in the horizontal position for 20-30 seconds. In both maneuvers the reference method to evaluate their response is the measurement of the changes in either cardiac output or stroke volume. A positive response according to most published literature is an increase by 10 to 15%.

Due to the difficulty and invasiveness of the measurement of SV, there are several clinical hemodynamic indexes available to evaluate or better predict volume responsiveness (see Table 1). Static indexes include the classic invasive and non-invasive pressure and volumetric parameters. Dynamic indexes include mainly those derived from heart-lung interactions during mechanical ventilation. Static indexes can in specific contexts be related to the patient's volume status measured for example by cardiac filling pressures, but have repeatedly proven to be very poor predictors of volume responsiveness and are therefore of little use to guide fluid therapy. Dynamic indexes such as pulse pressure or stroke volume variation have created great interest due to their simplicity and sound physiological basis. They have been shown to be far better predictors of fluid responsiveness than the static indexes in different populations of patients (Brandstrup B, Tonnesen H, Beier-Holgersen R, et al. Effects of intravenous fluid restriction on postoperative pulmonary complications: comparison of two perioperative fluid regiments: a randomized assessor-blinded multicenter trial Ann Surg 2003; 238: 641-8, Pinsky M R. Functional hemodynamic monitoring. Intensive Care Med 2002; 28: 386-8, Rosenberg A L, Dechert R E, Park P K, et al. Review of a large clinical series: association of cumulative fluid balance on outcome in acute lung injury; a retrospective review of the ARDSnet tidal volume study cohort. J Intensive Care Med 2009; 24: 35-46). However, it is currently acknowledged that their predictive value in ICU patients is much worse than previously thought and as low as only 2% of patients meet validity criteria to appropriately predict fluid responsiveness by means of these indexes (Mahjoub Y, Lejeune V, Muller L, Perbet S, Zieleskiewicz L, Bart F, Veber B, Paugam-Burtz C, Jaber S, Ayham A, et al.: Evaluation of pulse pressure variation validity criteria in critically ill patients: a prospective observational multicenter point-prevalence study. British Journal of Anaesthesia 2014, 112: 681-685.). The table below illustrates some clinically used static and dynamic indexes to assess cardiac preload and fluid responsiveness:

| Static Indexes | Measurement/ Comment | Dynamic Indexes | Measurement/ Comment |
| --- | --- | --- | --- |
| central venous pressure (CVP) | CVC/invasive continuous | systolic pressure variation (SPV) | arterial catheter/ invasive continuous |
| mean arterial pressure (MAP) | arterial catheter/ invasive continuous | pulse pressure variation (PPV) | arterial catheter/ invasive continuous |
| pulmonary artery occlusion pressure (PAOP) | PAC/invasive continuous | stroke volume variation (SVV) | arterial catheter/ invasive continuous |
| right atrial pressure (RAP) | equals CVP/invasive continuous | resp. variations in systolic pressure (RVSP) | arterial catheter/ invasive continuous |
| right ventricular end-diastolic volume (RVEDV) | PAC/invasive continuous | respiratory variability in SVC and or IVC | CVC/invasive continuous |
| global end-diastolic volume (GEDV) | PiCCO/ invasive discontinuous | aortic blood flow | Doppler, EchoC/ non-invasive semi-continuous |
| IVC/SVC diameter | EchoC/non-invasive discontinuous | | |
| left ventricular end-diastolic area (LVEDA) | EchoC-/non-invasive discontinuous | | | where CVC=central venous catheter, PAC=pulmonary artery catheter, SVC=superior vena cava, IVC=inferior vena cava, and EchoC=echo cardiography.

Now, two examples of interventions used in the assessment of fluid responsiveness according to prior art will be discussed in more detail.

The fluid challenge:
  The fluid challenge consists of the rapid intravenous infusion of a certain amount of fluid (either a crystalloid or a colloid) over a defined short period of time looking for an improvement in hemodynamic parameters, generally an increase in systolic blood pressure or more commonly in stroke volume (i.e. the volume of blood ejected per systolic contraction of the heart obtained from dividing cardiac output by heart rate). There is a lack of agreement as to what the absolute amount, type of fluid and rate of infusion that defines an adequate fluid challenge should be. Furthermore, as stated above, only 50% of critically ill patients respond favorably to a fluid challenge (responders), and such an irreversible intervention will always cause an unwanted, unnecessary and often harmful fluid overload in the remaining 50% of patients (non-responders).

The passive leg-rising maneuver:
  The passive leg-rising (PLR) maneuver is a reversible and dynamic strategy used to evaluate preload by raising the legs for 20-30 seconds and watching the hemodynamic response which is assessed clinically as an increase in cardiac output, stroke volume or systolic arterial pressure. The cardiac output increases in preload-dependent patients due to an auto-transfusion of blood from legs to the heart. The advantage is that no extra fluid is infused thereby minimizing the risks of a potentially harmful fluid overload. Therefore, the PLR maneuver can be performed repeatedly. There are however also limitations in this intervention. First it cannot usually be performed in the operating theater and not all ICU patients can be subjected to this maneuver. Furthermore, the accuracy is poor in patients with increased intra-abdominal pressure. Finally, it is dependent on the patient's actual volemic state (amount of circulating blood volume) so that the expected effect is reduced and more difficult to interpret in patients with severely reduced volemia.

Now, some examples of assessments and indexes used in assessments of fluid responsiveness according to prior art will be described in more detail.

Clinical evaluation:
  Skin turgor, patient's vitality and cognitive status, urine output, blood pressure and heart rate, peripheral perfusion and capillary refilling time are nonspecific, subjective and unreliable clinical signs for determining fluid responsiveness (Marik P E, Monnet X, Teboul J L. Hemodynamic parameters to guide fluid therapy. Ann Intensive Care 2011; 1: 1., Cavallaro et al. Functional hemodynamic monitoring and dynamic indices of fluid responsiveness. Minerva Anestesiol 2008; 74: 123-135, Vincent J L, et al. Fluid challenge revisited. Crit Care Med 2006; 34: 1333-1337). This is especially true for those patients who are not frankly hypovolemic and have a slight to moderate preload-dependency.

Hemodynamic indexes:
  The pressure-based parameters listed in the above table are frequently used clinically to estimate a patient's preload status. However, their predictive value for fluid responsiveness is very limited because ventricular or vascular compliance is not linear in most clinical scenarios and hence render pressure-related parameters bad surrogates of intravascular volume. Thus, an increment/decrement in those intravascular pressures typically does not fit with the respective changes in intravascular volume or ventricular preload. Additionally, changes in cardiac transmural pressure as seen for example after a myocardial infarction or due to high intrathoracic pressure can be misinterpreted as an excessive volemia in a hypovolemic patient when using these static parameters. Static parameters are in general more accurate estimates of preload but are either invasive (RVEDV, GEDV), subjective (LVEDA) or only assessed intermittently (GEDV, LVEDA).

Dynamic hemodynamic indexes:
  Pulse pressure variation (PPV) and stroke volume variation (SW) refer to the change in the amplitude of the pulse pressure waveform and in the amount of volume of blood ejected by the left ventricle during the mechanical respiratory cycle, respectively. The reduction in preload and increase in afterload seen during the inspiratory positive pressure respiratory cycle manifests as a decrease in the amplitude of the pulse pressure waveform or stroke volume (measured as the area under the systolic portion of the systemic arterial pressure waveform) during the expiratory phase. The relative difference between the inspiratory and expiratory values of these parameters defines the PPV and SSV. In preload-dependent patients the inspiratory increase in intrathoracic pressure during positive pressure mechanical inspiration has a much greater effect on the pulse pressure amplitude and stroke volume than in normovolemic patients. In general, it is established that a PPV and/or SSV higher than 13% identifies volume responders or preload-dependent patients. The advantage of these parameters is that in theory they indicate the state of volume responsiveness of a patient continuously, without the need to measure cardiac output or an exploratory fluid challenge. However, there are several important limitations of these indexes. Their performance is influenced by the ventilator settings applied (generally needing larger tidal volumes than the ones recommended for lung protective ventilation) and they are only reliable in passive ventilatory conditions without any spontaneous breathing activity of the patient. Furthermore, they are affected by many confounders and thus not reliable in several common conditions seen in ICU patients such as arrhythmias or pulmonary hypertension. Not surprisingly, in a recent clinical prospective evaluation only 3% of ICU patients met validity criteria to use PPV and SW to predict volume responsiveness.

Other dynamic indexes:
  The respiratory changes in aortic flow velocity assessed by Doppler echocardiography predicted fluid responsiveness in mechanically ventilated patients (Feissel M, et al. Respiratory changes in aortic blood velocity as an indicator of fluid responsiveness in ventilated patients with septic shock. Chest 2001; 119: 867-873). Similarly, cyclic changes in superior and inferior vena cava diameter measured by echography have been used to detect preload dependency in mechanically ventilated patients. A distensibility index was proposed to reflect such changes (Barbier C, et al. Respiratory changes in inferior vena cava diameter are helpful in predicting fluid responsiveness in ventilated septic patients. Intensive Care Med 2004; 30: 1740-1746). A limitation of these techniques is the availability of appropriate ultrasound equipment, the intermittent and subjective nature of the measurement and the need of an expert in the field. The end-expiratory occlusion test consists of an interruption of mechanical insufflation by an end-expiratory occlusion, which can increase cardiac preload sufficiently to be used to predict fluid responsiveness. If the maneuver increases cardiac output by more than 15% the patient is considered a fluid responder.

From the above discussion, it can be seen that there is a desire for a novel technique for predicting fluid responsiveness which meets the following objectives:
  reversible, meaning that the clinical test should not cause any lasting potential deleterious effect on the cardiovascular system or systemic organs. Techniques such as the above discussed fluid challenge may be associated with severe complications in non-responding patients leading to unwanted and potential harmful fluid overload.

dynamic, meaning that the novel technique causes the cardiovascular system to be somewhat stressed for a brief moment to expose preload dependency. Such dynamic maneuvers have repeatedly been shown to be more accurate than static indexes for determining fluid responsiveness.

non- or minimally invasive, meaning that any hemodynamic parameters used in the assessment of fluid responsiveness should be ideally obtained without penetrating the skin barrier or intruding the cardiovascular system with catheters or other devices, thereby avoiding serious complications such as bleeding or infections.

real-time based, meaning that any monitored parameters used in the assessment of fluid responsiveness must have a time resolution which allows the detection of any hemodynamic change on a continuous or near-continuous basis, e.g. on a beat-by-beat or breath by breath basis.

SUMMARY OF THE INVENTION

It is an object of the invention to provide a method and apparatus for predicting fluid responsiveness of a subject undergoing mechanical ventilation.

It is another object of the invention to provide such a method and apparatus that eliminate or at least mitigates one or more of the shortcomings associated with prior art described above.

It is yet another object of the invention to provide a method and apparatus that enable an easy and reliable prediction of fluid responsiveness of a mechanically ventilated subject at the bedside of the subject in clinical practice.

It is yet another object of the invention to provide a method and apparatus that enable a non-invasive prediction of fluid responsiveness of a mechanically ventilated subject.

According to one aspect of the invention, a method for prediction of fluid responsiveness of a subject connected to a breathing apparatus capable of providing mechanical ventilation to the subject includes the steps of:

monitoring at least one parameter indicative of a degree of carbon dioxide elimination ($VCO_2$) of the subject;

applying a PEEP maneuver in which the positive end-expiratory pressure (PEEP) applied to the subject is changed from a first PEEP level to a second PEEP level, and predicting the fluid responsiveness of the subject based on a change in said at least one monitored parameter following said change in PEEP.

The inventive method is non-invasive without intravascular catheters, fully reversible without the need of any fluid infusion, dynamic (change in PEEP) with a real-time monitoring of the $VCO_2$ response (change in $VCO_2$) to the change in PEEP. This particular combination of events related to the $CO_2$ kinetics allows an easy diagnosis of preload dependency at the bedside without the need of advanced invasive and expensive hemodynamic monitoring used in systems according to prior art.

Further, the inventive method differentiates the alterations in pulmonary perfusion caused by changes in preload from the ones due to changes in right ventricle contractility. This is because PEEP does not have any effect on myocardial contractility itself but it affects right ventricular stroke volume and pulmonary perfusion minimally in normovolemic patients but highly in hypovolemic patients. In other words, a change in PEEP, e.g. a stepwise increment of PEEP, will only alter hemodynamics in those patients who are preload-dependent.

According to another embodiment of the method, the change in said at least one monitored parameter is determined as the difference between a substantially steady state level of said parameter prior to said change in PEEP (i.e. a baseline level), and a new substantially steady state level of said parameter after said change in PEEP.

According to another embodiment of the method, said change is determined based on the difference between at least one pre-PEEP adjustment value of said at least one monitored parameter obtained prior to said change in PEEP, and at least one post-PEEP adjustment value of said at least one monitored parameter obtained after said change in PEEP.

According to another embodiment of the method, said at least one post-PEEP adjustment value of the monitored parameter is obtained 10-120 seconds, preferably 30-90 and most preferably 45-75 seconds after said change in PEEP. In a preferred embodiment, the at least one post-PEEP adjustment value is obtained about 1 minute after said change in PEEP. This is because $VCO_2$ in most ventilated subjects, after a suitable change in PEEP of approximately 5 $cmH_2O$, has reached a substantially steady state about 1 minute after the change.

According to a further embodiment of the method, the monitored parameter is the actual $VCO_2$ of the subject and the prediction is thus based on a change in $CO_2$ elimination ($\Delta CO_2$) of the subject following said change in PEEP. The $VCO_2$ of the subject may be determined from measured flow or volume of expiration gas exhaled by the subject, and a measured parameter indicative of the presence of $CO_2$ in said expiration gas, such as the partial pressure, concentration or volume of $CO_2$ in the expiration gas. In a preferred embodiment, $VCO_2$ of the subject is determined through volumetric capnography.

According to another embodiment of the method, the prediction involves a step of judging the ventilated subject to be fluid-responsive if the change in $CO_2$ elimination ($\Delta VCO_2$) exceeds a predetermined threshold value. Said threshold value should preferably be at least 5%, more preferably at least 10% and even more preferably at least 11% of baseline $VCO_2$, i.e. the steady state level of $VCO_2$ prior to the change in PEEP.

Preferably, the PEEP maneuver is performed by a change in PEEP of at least 5 $cmH_2O$. In one embodiment, the change in PEEP is a stepwise increment or decrement of PEEP of 5 or 10 $cmH_2O$. In a preferred embodiment, the change in PEEP is a stepwise increment of PEEP of 5 or 10 $cmH_2O$.

According to another embodiment of the method, the step of changing the PEEP in order to determine the change in the at least one monitored $VCO_2$-related parameter is preceded by a preconditioning maneuver in which a sequence of breaths of increased pressure and increased PEEP is provided to the subject. This has the effect of minimizing any significant lung re-expansion effect during the PEEP challenge (i.e. during ventilation at the changed PEEP level) and so serves to increase the accuracy in the prediction of fluid responsiveness.

The method may further comprise a step of visually and/or audibly signaling to an operator of a breathing apparatus carrying out the method whether or not the subject is judged to be fluid responsive or not based on the result of said prediction. This may for example be achieved through the display of an indicator indicating whether the subject is judged to be fluid responsive or not on a display unit of said breathing apparatus.

In some embodiments, the method may involve the steps of calculating a fluid responsiveness index for the subject based on the change in said at least one monitored parameter following said change in PEEP, and visually and/or audibly communicating said fluid responsiveness index to an operator of the breathing apparatus. This fluid responsiveness index may be a multiple level index indicating the degree of fluid responsiveness of the subject on a multi-level scale, e.g. a scale between 1-5 or 1-10.

In an embodiment, hereinafter referred to as the dose response embodiment, the method includes a step of predicting a degree of fluid responsiveness of the subject based on the change in PEEP required to cause the at least one monitored parameter to exceed a certain predetermined threshold value. The dose response embodiment may involve the steps of stepwise changing the PEEP applied to the subject until the at least one monitored parameter exceeds said threshold value (e.g. 11% of baseline $VCO_2$), and predicting a degree of fluid responsiveness of the subject based on the change in PEEP required to make the at least one monitored parameter exceed the threshold value, that is to say based on the "dose" required to obtain a certain response in the monitored parameter. For example, a patient for which the change in monitored $VCO_2$ value exceeds a threshold value of e.g. 11% of baseline $VCO_2$ following a change in PEEP of 5 $cmH_2O$ (e.g. a change from 5 to 10 $cmH_2O$) may be identified as a severely hypovolemic patient, while a patient for which the change in monitored $VCO_2$ does not exceed said threshold value unless the change in PEEP is at least 10 $cmH_2O$ may be identified as a moderately hypovolemic patient. A patient for which the monitored $VCO_2$ value changes only slightly (i.e. change in $VCO_2$<threshold value) in response to a change in PEEP of e.g. 10 $cmH_2O$ may be identified as a mildly hypovolemic patient. The amount of intravascular fluid provided to a patient that has been judged to be fluid responsive using the above described principles may advantageously be selected in dependence of the predicted degree of fluid responsiveness of the patient using the proposed dose response procedure. Thereby, the amount of fluid can be selected based on a non-invasive test indicating whether the ventilated patient suffers from mild, moderate or severe hypovolemia.

Thus, the above mentioned step of predicting the fluid responsiveness of the subject based on a change in said at least one monitored parameter following said change in PEEP may comprise a step of predicting a degree of fluid responsiveness of the subject based on any or both of: i) the change in the at least one monitored parameter following a certain predetermined change in PEEP applied to the subject, and ii) the change in PEEP required to make the change (in magnitude) in the at least one monitored parameter exceed a certain threshold value.

Another aspect of the present invention is a non-transitory, computer-readable data storage medium encoded with programming instructions for prediction of fluid responsiveness of a subject connected to a breathing apparatus providing mechanical ventilation to the subject. The programming instructions are computer-readable code that, when executed by a processor of the breathing apparatus, causes the breathing apparatus to perform the method according to any of the above described embodiments.

Thus, according to one embodiment, the computer code, when executed by the processor, causes the breathing apparatus to:

monitor at least one parameter indicative of a degree of $VCO_2$ of the subject;

change a PEEP applied to the subject from a first PEEP level to a second PEEP level, and predict the fluid responsiveness of the subject based on a change in said at least one monitored parameter following said change in PEEP.

Another aspect of the present invention is a breathing apparatus for prediction of fluid responsiveness of a subject connected to the breathing apparatus. The breathing apparatus includes:

a PEEP regulator, e.g. an expiratory valve for regulating a flow of expiration gas exhaled by the subject, configured to regulate the PEEP applied to the subject;

a control processor configured to control the PEEP regulator and to monitor at least one parameter indicative of a degree of $VCO_2$ of the subject, wherein said control processor is configured to control said PEEP regulator to change the PEEP applied to the subject from a first PEEP level to a second PEEP level, and to predict the fluid responsiveness of the subject based on a change in said at least one monitored parameter following said change in PEEP.

The breathing apparatus further has a sensor arrangement, such as a capnograph and preferably a volumetric capnograph, configured to measure the flow or volume of expiration gas exhaled by the subject, and a parameter indicative of the presence of $CO_2$ in said expiration gas, such as the partial pressure, concentration or volume of $CO_2$ in the expiration gas. In one embodiment, the control processor is configured to calculate the $VCO_2$ of the subject from said measured parameters, whereby the $VCO_2$ of the subject is the parameter that is monitored and used by the control processor in the prediction of fluid responsiveness.

In another embodiment, the control processor is configured to determine said change in the at least one monitored parameter as the difference between a substantially steady state level of said parameter prior to said change in PEEP, and a new substantially steady state level of said parameter after said change in PEEP.

In another embodiment, the control processor is configured to determine the change in said at least one monitored parameter based on the difference between at least one pre-PEEP adjustment value of said at least one monitored parameter obtained prior to said change in PEEP, and at least one post-PEEP adjustment value of said at least one monitored parameter obtained after said change in PEEP, wherein said at least one post-PEEP adjustment value of the monitored parameter is obtained 10-120 seconds after said change in PEEP.

The monitored parameter indicative of the carbon dioxide elimination of the subject may, according to one embodiment, be the actual carbon dioxide elimination itself, and the control processor may be configured to predict the fluid responsiveness of the subject based on a change in the carbon dioxide elimination ($\Delta VCO_2$) of the subject following the change in PEEP.

In another embodiment, the control processor is configured to judge the subject to be fluid-responsive if said change in $CO_2$ elimination ($\Delta VCO_2$) exceeds a predetermined threshold value.

In another embodiment, the control processor is configured to carry out a preconditioning maneuver by providing a sequence of breaths of increased pressure and increased PEEP to the subject prior to changing the PEEP in order to determine the change in said at least one monitored parameter.

In another embodiment, the control processor is configured to visually and/or audibly signal to an operator of the breathing apparatus whether or not the subject (3) is deemed to be fluid responsive based on the result of said prediction.

In another embodiment, the control processor is configured to calculate a fluid responsiveness index for said subject based on the change in said at least one monitored parameter following said change in PEEP, and to visually and/or audibly communicate said fluid responsiveness index to an operator of the breathing apparatus.

DESCRIPTION OF THE PREFERRED EMBODIMENTS

Figure 2:
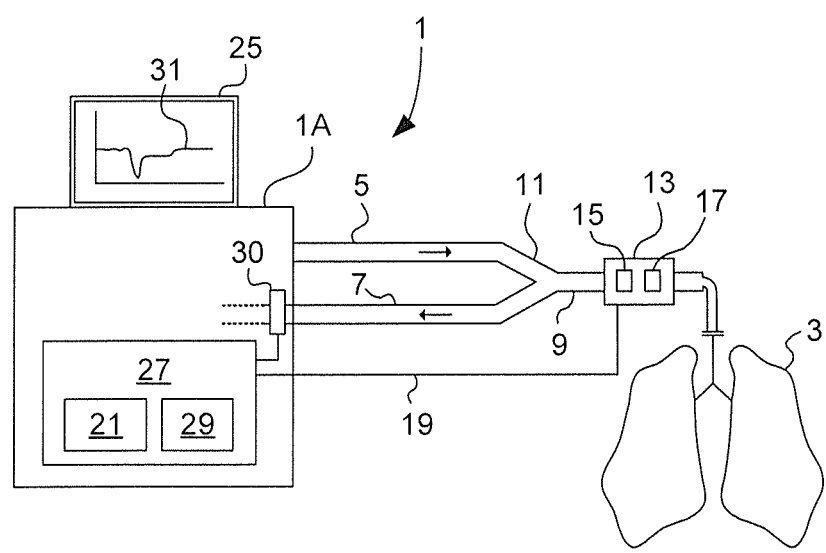
FIG. 2 illustrates schematically a breathing apparatus according to an embodiment of the present disclosure, configured for prediction of fluid responsiveness of a ventilated subject.

FIG. 2 illustrates a breathing apparatus 1 according to an exemplary embodiment of the invention. In this embodiment the breathing apparatus is a ventilator for providing ventilatory treatment to a patient 3 connected to the ventilator. The ventilator is connected to the patient 3 via an inspiratory line 5 for supplying breathing gas to the patient 3, and an expiratory line 7 for conveying expiration gas away from the patient 3. The inspiratory line 5 and the expiratory line 7 are connected to a common line 9, via a so called Y-piece 11, which common line is connected to the patient 3 via a patient connector, such as an endotracheal tube.

A capnograph 13 configured for volumetric capnography measurements is arranged in the proximity of the airways opening of the patient 3. In this exemplary embodiment, the capnograph 13 is arranged in the common line 9 and exposed to all gas exhaled and inhaled by the patient 3. The capnograph 13 comprises a flow or volume sensor 15 for measuring at least the flow or volume of expiration gas exhaled by the patient 3, and a $CO_2$ sensor 17 for detecting the presence of $CO_2$ in at least said expiration gas. To this end, the capnograph 13 may be configured to measure any suitable parameter indicative of alveolar $CO_2$, such as the partial pressure of $CO_2$ ($PACO_2$), the $CO_2$ concentration or the volume of $CO_2$ in the expiration gas. Typically but not necessarily the capnograph 13 is configured to measure also the flow or volume of inspiration gas inhaled by the patient 3, and a parameter indicative of the presence of $CO_2$ in the inspiration gas.

The capnograph 13 is connected to the ventilator via a wired or wireless connection 19, and configured to transmit the flow or volume and $CO_2$ measurements to the ventilator for further processing by a processor 21 of the ventilator. The ventilator is preferably configured to generate a volumetric capnogram from the flow and $CO_2$ measurements received from the capnograph 13, and, additionally, to display the volumetric capnogram on a display 25 of the ventilator.

The processor 21 is typically part of a control processor 27 of the ventilator, which control processor 27 further comprises a non-volatile memory or data carrier 29 storing a computer program that causes the processor 21 to predict the fluid responsiveness of the patient 3 in accordance with the principles of the present invention, typically based on the flow or volume and $CO_2$ measurements received from the capnograph 13, as will be described in more detail below.

The control processor 27 is further configured to control an expiratory valve 30 of the breathing apparatus according to the instructions of said computer program in order to adjust a positive end-expiratory pressure (PEEP) applied to the ventilated subject 3 as required in order to predict the fluid responsiveness of the subject 3 in accordance with the principles of the present disclosure.

The ventilator is further configured to display information related to the predicted fluid responsiveness of the patient 3 on the display 25. Preferably, said information comprises an indicator indicating whether the patient 3 is deemed to be fluid responsive (i.e. a fluid responder) or if the patient 3 is deemed not to be fluid responsive (i.e. not to be a fluid responder). The ventilator may further be configured to display, on the display 29, a $CO_2$ elimination ($VCO_2$) trend curve 31, illustrating changes in $CO_2$ elimination of the patient 3 over time. The $VCO_2$ trend curve 31 will be described in more detail below with reference to FIG. 4.

The ventilator 1 further comprises a user interface through which an operator of the ventilator can control the operation of the ventilator 1. The user interface may comprise the display 25, which may include a touch-screen allowing the operator to input control commands to the ventilator via the display 25, and/or a control panel (not shown) including one or more electro-mechanical actuators through which the operator may control the operation of the ventilator 1. In one embodiment, the ventilator 1 is configured to allow the ventilator operator to input, via said user interface, a command instructing the ventilator 1 to carry out a fluid responsiveness check in which the fluid responsiveness of the patient 3 currently connected to the ventilator 1 is predicted according to the principles of the invention, which principles will now be described with reference to FIGS. 2-5.

The rationale behind the proposed technique to assess fluid responsiveness combines the effects of positive pressure ventilation and in particular end-expiratory pressure (PEEP) on hemodynamics and lung perfusion, and how they affect body kinetics of $CO_2$.

Positive Pressure Ventilation and PEEP

The incidence of preload-dependency in positive pressure mechanically ventilated patients is high[5]. This is related to the fact that a positive airway pressure is maintained throughout the respiratory cycle. This is in great opposition to normal breathing where transpulmonary pressure remains negative during the inspiratory phase, literally sucking in blood from the systemic circulation into the thorax and to the right heart. This altered physiology during positive pressure ventilation dramatically changes the cyclic effect of breathing on hemodynamics. It interferes with venous return as the major veins, the superior and inferior cava veins, entering the thoracic cavity are compressed by the positive intrathoracic pressure. This in turn is the cause of a reduction in RV stroke volume that has an immediate effect on LV stroke volume due to the in series configuration of the cardiovascular system. This effect is clinically seen as a reduction in cardiac output and mainly systolic blood pressure. This is the primary major determinant of the fluid dependency of virtually all newly intubated and mechanically ventilated patients who require variable amounts of intravenous fluid to compensate for this effect. There are however other mechanisms that govern cardio-pulmonary interactions that reduce preload or increase afterload thereby compromising RV function and hence hemodynamics in ventilated patients. These negative effects will be understandably larger the higher the pressures applied during mechanical ventilation and the lower the volemia of the patient. They can in general be summarized as follows:

Reduction in Venous Return:
  a. compression of the large veins (superior and inferior cava veins) at their entrance into the thoracic cavity
  b. low right atrial compliance leading to increased right atrial pressure that reduces the venous return pressure gradient Increased RV Afterload:
  a. increase in alveolar pressure during positive pressure ventilation and PEEP that compress the pulmonary alveolar capillaries thereby increasing pulmonary vascular resistance
  b. pulmonary collapse that reduces the cross-sectional area of pulmonary capillaries and reduces total lung volume, both leading to increased pulmonary vascular resistance The Effect of PEEP on Hemodynamics Of particular interest and subject of extensive study is the effect of PEEP on hemodynamics. The use of PEEP elevates the "working pressure" of the respiratory system which will change from the "normal" atmospheric pressure that is physiologically maintained during respiratory resting conditions, that is, at end-expiration, to the level determined by PEEP. This directly affects all other changes observed during the mechanically delivered cycle and will cause an additional cardiovascular stress that is not relieved from the positive pressure during expiration. In summary, the above mentioned negative hemodynamic effects will be enhanced by the addition of PEEP.

Due to its known hemodynamic effects, a PEEP challenge can be a valuable alternative intervention to assess the dynamic interaction of this imposed stress on the cardiovascular system and different hemodynamic or perfusion variables. A PEEP challenge can be defined as a controlled step change (e.g. increase) in the level of PEEP, which step change is a change of sufficient magnitude under defined ventilatory conditions. The magnitude of the step change depends on the variable that is used to assess it, the status of the lung and on the volemia as in severely hypovolemic patients an excessive increase in PEEP can lead to dangerous decreases in cardiac output.

$CO_2$ as a Marker of Pulmonary Perfusion

The $CO_2$ follows well known kinetics in the body, consisting of four steps:

Step I) Metabolism: the metabolic production of $CO_2$ by body cells;
Step II) Transport by circulation: $CO_2$ transport by venous blood to the right heart and pulmonary circulation;
Step III) Diffusion: $CO_2$ diffusion from pulmonary capillaries into alveoli, and
Step IV) Alveolar ventilation: $CO_2$ elimination by alveolar ventilation.

Figure 3:
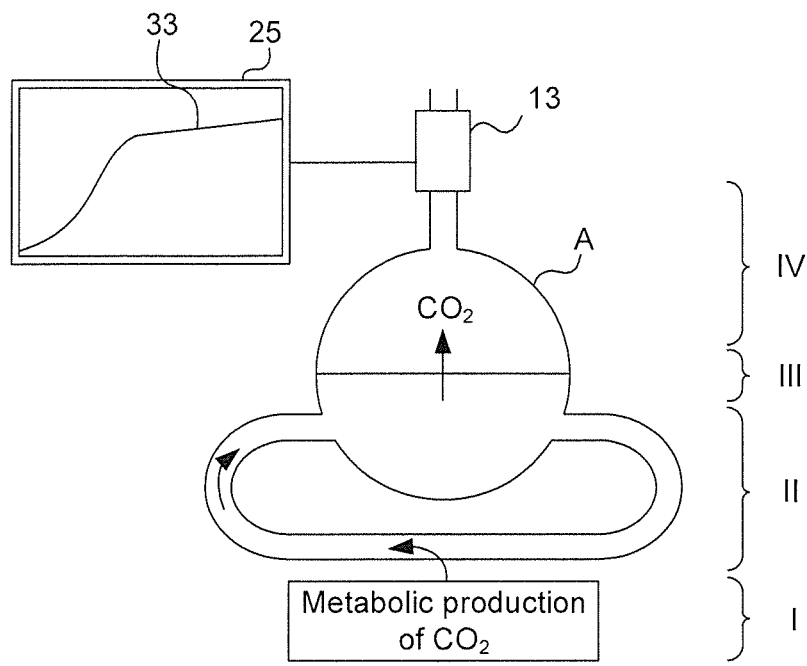
FIG. 3 illustrates schematically a model of pulmonary gas exchange taking place in the alveoli of the lungs of a subject.

Such $CO_2$ kinetics can be monitored non-invasively in real-time by volumetric capnography; i.e. the graphical recording of expired volume of $CO_2$ in one breath. This is shown in FIG. 3, schematically illustrating the metabolic production of $CO_2$ by body cells taking place in a first step I, the $CO_2$ transport by venous blood to the lungs taking place in a second step II, the $CO_2$ diffusion from pulmonary capillary into alveoli taking place in a third step III, and the $CO_2$ elimination by alveolar ventilation taking place in a fourth step IV. In FIG. 3, reference numeral A denotes an element representing the alveoli and pulmonary capillaries in which diffusion takes place, whereas reference numeral 13 denotes the capnograph in FIG. 1, connected to the display 25 displaying a volumetric capnogram 33 in which $PACO_2$ (y-axis) is plotted against volume of expired gas (x-axis) for the last expiration of the patient 3. The main variable of volumetric capnography is the area under the curve, representing the amount of $CO_2$ eliminated in one single breath. This value when multiplied by the respiratory rate (RR) yields the pulmonary elimination of $CO_2$ per unit of time, e.g. one minute ($VCO_2$).

The only way $CO_2$ is eliminated from the body is by following the above sequential and unidirectional kinetics. Therefore, $VCO_2$ is a good marker of pulmonary blood flow provided that metabolism (step 1) and alveolar ventilation (step 4) remain constant as observed commonly in mechanically ventilated patients. This fact constitutes the basis of non-invasive determination of effective pulmonary blood flow using Fick's principle and the partial rebreathing $CO_2$ technique. As pulmonary blood flow depends on both volemia (or preload) and right ventricular contractility, any hypovolemia or decrement in contractility will decrease the elimination of $CO_2$ and vice versa (Michard F, Chemla D, Richard C, et al. Clinical use of respiratory changes in arterial pulse pressure to monitor the hemodynamic effects of PEEP. Am J Respir Crit Care Med 1999; 159: 935-9, Lambert P, Sloth E, Smith B, Hansen L K, Koefoed-Nielsen J, Tonnesen E, Larsson A. Does a positive end-expiratory pressure-induced reduction in stroke volume indicate preload responsiveness? An experimental study. Acta Anaesthesiol Scand 2007; 51: 415-25).

A few publications have described the use of end-tidal $CO_2$ ($PETCO_2$), i.e. the end concentration/partial pressure of $CO_2$ in one breath, as a non-invasive parameter to assess dynamic hemodynamic changes in response to different interventions (Lambert P, Sloth E, Smith B, Hansen L K, Koefoed-Nielsen J, Tonnesen E, Larsson A. Does a positive end-expiratory pressure-induced reduction in stroke volume indicate preload responsiveness? An experimental study. Acta Anaesthesiol Scand 2007; 51: 415-25, Tusman G, Areta M, Climente C, et al. Effect of pulmonary perfusion on the slopes of single-breath test of $CO_2$. J Appl Physiol 2005; 99: 650-5). These studies are based on the above described kinetics of $CO_2$ in the body and were performed with standard time-based capnography instead of the proposed volumetric capnography. Thus, Monge et al. and Monnet et al. showed that $PETCO_2$ can be used to detect preload dependency in mechanically ventilated patients (Guzman J A, Lacoma F J, Najar A, et al. End-tidal partial pressure of carbon dioxide as a non-invasive indicator of systemic oxygen supply dependency during hemorrhagic shock and resuscitation. Shock 1997; 8: 427-31, Gudipati C V, Weil M H, Bisera J, Deshmukh H G, Rackow E C. Expired carbon dioxide: a non-invasive monitor of cardiopulmonary resuscitation. Circulation 1988; 77: 234-239.). They applied a PLR maneuver to stress the cardiovascular system and compared the hemodynamic response seen in $PETCO_2$ versus a standard invasive measurement of cardiac index.

The good correlation found between these parameters confirms the clinical role of $CO_2$ for hemodynamic assessment.

However, $VCO_2$ is believed to be a better parameter than $PETCO_2$ to determine changes in pulmonary blood flow because $VCO_2$ includes also a dimension of "flow" (i.e. volume per time) that depends on the ventilation and the amount of blood in contact with the alveolar-capillary membrane. This means that $VCO_2$ is directly proportional to both pulmonary perfusion and ventilation. Therefore, any change in pulmonary blood flow caused by a modification in preload will be detected by changes in $VCO_2$. Contrarily, $PETCO_2$ is a "partial pressure" that depends mainly on the passive diffusion of $CO_2$ from venous blood and is inversely related to alveolar ventilation. These features render $PETCO_2$ less sensitive than $VCO_2$ to detect changes in pulmonary blood flow caused by modifications in preload.

Prediction of Fluid Responsiveness Based on PEEP Adjustment-Induced Changes in $CO_2$ Elimination The present disclosure presents a new technique for detecting preload-dependent patients based on the analysis of $VCO_2$, preferably by means of volumetric capnography. This technique combines a fully reversible and dynamic maneuver to stress the cardiovascular system (a stepwise and brief increment/decrement of PEEP) together with non-invasive and real-time monitoring of the hemodynamic response ($VCO_2$ assessed by volumetric capnography).

Some of the key features of the proposed method for detection of fluid responsiveness are hence the steps of introducing a change in PEEP of a ventilated patient and determining the change in $CO_2$ elimination following said change in PEEP.

As mentioned above, the proposed technique differentiates the alterations in pulmonary perfusion caused by changes in preload from the ones due to changes in right ventricle contractility because PEEP has no effect on myocardial contractility in normovolemic patients but high effect on the hemodynamics in hypovolemic patients. Thus, a change in PEEP, e.g. a stepwise increment of PEEP, will only alter hemodynamics in those patients who are preload-dependent.

However, the effects of PEEP are not always easy to predict depending on the underlying status of the lung. An increase in PEEP concomitantly increases the inspiratory pressure and this can lead to recruitment of partially collapsed units. This will have two principal consequences: 1) it will increase the capillary cross-sectional area as it will also recruit the capillaries perfusing those regions and 2) will improve the regional alveolar tension of oxygen of these newly recruited units, reverting the hypoxic pulmonary vasoconstriction effect. Both effects will tend to improve RV function as they will reduce pulmonary vascular resistance and hence RV afterload. This in turn will blur the hemodynamic response of a step increase in PEEP as it will oppose the expected decrease in cardiac output. The specificity and sensitivity of the PEEP challenge to assess the hemodynamic status will be inevitably reduced as long as the extent of such inadvertent recruitment effects cannot be predicted. One possible way to overcome this limitation is to perform a preceding lung preconditioning maneuver to re-expand collapsed airways and easily re-expandable lung regions—a sort of homogenization of the lung volume. This preconditioning maneuver consists of a sequence of a few breaths at higher pressures, i.e. a sequence of breaths of increased pressure compared to baseline ventilation. Preferably but not necessarily said breaths of increased pressure are also delivered at higher PEEP, i.e. at a PEEP level that is increased compared to baseline ventilation. The aim is to minimize any significant lung re-expansion effect during the PEEP challenge.

Preferably, the dynamic maneuver consist first of a short preconditioning maneuver and, after a short stabilization period, of a step increase in PEEP above the baseline PEEP for one minute after which it is again reduced to the baseline value.

It should be noted that the above described preconditioning maneuver is not a lung recruitment maneuver in the conventional meaning of the term but a preconditioning maneuver serving to homogenize the lung volume of the patient. For example, in some circumstances, the preconditioning maneuver may consist of the application of 10 breaths at an increased tidal volume of approximately 10 ml/kg, e.g. corresponding to a pressure increase of 20-30% compared to baseline ventilation, and a PEEP level that is increased with 5 $cmH_2O$ compared to baseline ventilation.

Figure 4:
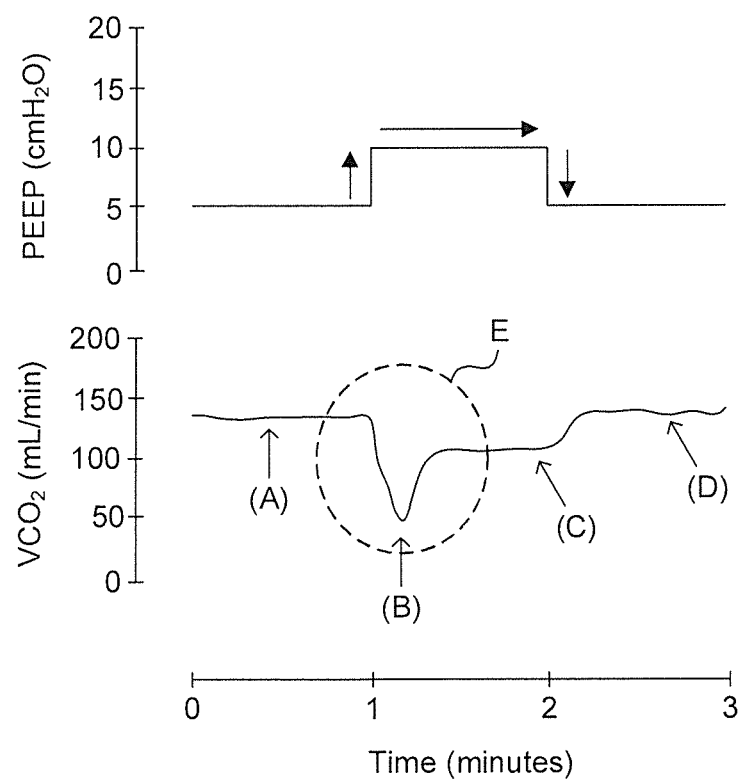
FIG. 4 show graphs illustrating changes in carbon dioxide elimination of a ventilated patient before, during and after being subject to changes in positive end-expiratory pressure.

FIG. 4 shows the recording of PEEP and $VCO_2$ during the proposed maneuver for predicting fluid responsiveness of a patient according to the principles of this disclosure (not to be confused with the above discussed preconditioning maneuver that is advantageously carried out prior to the proposed maneuver for predicting fluid responsiveness of the subject)

Initially, a baseline $VCO_2$ (A), i.e. the $VCO_2$ level during baseline PEEP ventilation, is determined before the maneuver. Later on, the sudden increment in PEEP by 5 $cmH_2O$ retains a volume of gas within lungs and thus $VCO_2$ decreases due to a transient dilution of the $CO_2$ stored within lungs by $CO_2$-free inspired gases (B). After a while, a phase of a new equilibrium in expired $CO_2$ is reached (C) (at the end of the second minute in the graph) and the last four breaths in this phase are analyzed. The PEEP value then returns to baseline PEEP, causing $VCO_2$ to return to baseline $VCO_2$ (D).

Figure 5:
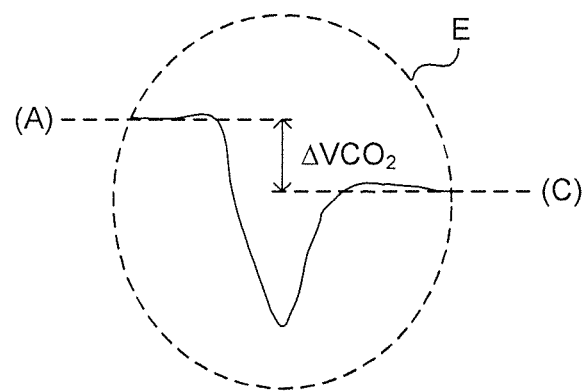
FIG. 5 shows a part of the graph illustrating changes in carbon dioxide elimination of a ventilated patient, illustrated in FIG. 4.

FIG. 5 illustrates the part of the $VCO_2$ curve denoted by reference numeral E in FIG. 4, i.e. the part of the $VCO_2$ curve illustrating the change in $VCO_2$ following the change in PEEP. The difference or change in $VCO_2$ between baseline $VCO_2$ (A) and the level of $VCO_2$ during the new steady state of $VCO_2$ (C) following the change in PEEP, hereinafter referred to as $\Delta VCO_2$, is, according to one embodiment of the invention, the parameter used to predict fluid responsiveness of a ventilated patient. The parameter $\Delta VCO_2$ thus represents the difference in $VCO_2$ between points (A) and point (C) in FIG. 4, and the magnitude of $\Delta VCO_2$ is the (positive or negative) change in $VCO_2$ following the change in PEEP.

If the magnitude of $\Delta VCO_2$ exceeds a predetermined threshold value, the ventilated patient is judged to be a "responder", i.e. a preload-dependent and thus fluid responsive patient. If, on the other hand, the magnitude of $\Delta VCO_2$ does not exceed said predetermined threshold value, the patient is considered a "non-responder" who is judged not to be fluid responsive.

Preferably, the threshold value for the magnitude of $\Delta VCO_2$ is set to approximately 10% of baseline $VCO_2$, and even more preferably to approximately 11% of baseline $VCO_2$. Thus, according to one embodiment of the invention, the ventilated patient is judged to be fluid responsive if $\Delta VCO_2 \geq 11\%$ of baseline $VCO_2$. Clinical data show that a threshold value of 11% of baseline predicts fluid responsiveness with 97% sensitivity and 95% specificity It should be noted that although FIGS. 4 and 5 illustrate an embodiment in which the proposed PEEP maneuver involves an increase in PEEP applied to the patient (causing a decrease in $VCO_2$ and thus a negative $\Delta VCO_2$), the PEEP maneuver may just as well involve a decrease in PEEP (causing an increase in $VCO_2$ and thus a positive $\Delta VCO_2$).

The proposed maneuver is preferably performed during conditions of controlled mechanical ventilation (preferably in a volume, constant flow mode) and assumes no changes in the ventilatory (constant tidal volume and respiratory rate) and metabolic conditions of the patient during the approximately one minute of measurements. Therefore, it might be advantageous to ventilate the patient in a volume controlled mode of ventilation during the maneuver, as opposed to pressure controlled ventilation modes in which the tidal volume of the patient may vary in between breaths. Thus, it may be advantageous to switch operational mode of the breathing apparatus 1 from a current non-volume controlled mode of ventilation to a volume-controlled mode of ventilation prior to conducting the proposed method for prediction of fluid responsiveness.

Figure 6:
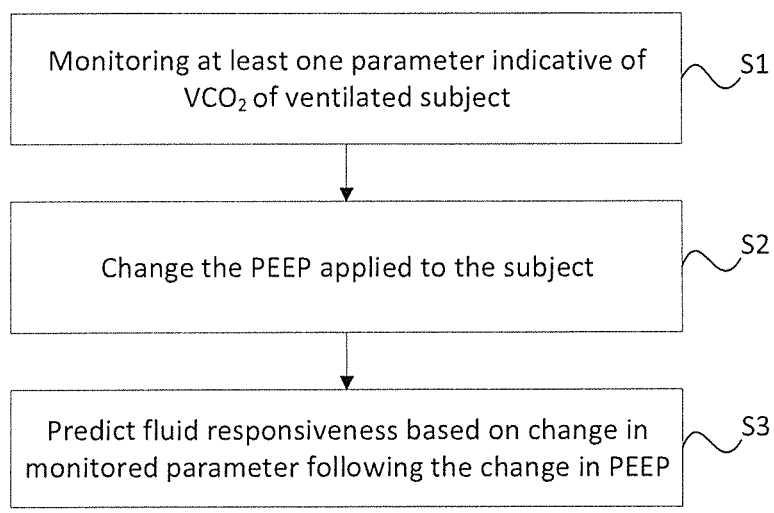
FIG. 6 shows a flowchart illustrating a method for prediction of fluid responsiveness according to an embodiment of the present invention.

FIG. 6 shows a flowchart illustrating a method for prediction of fluid responsiveness according to an embodiment of the present disclosure.

The method is typically performed by a breathing apparatus, such as the ventilator in FIG. 2, through the execution of a computer program causing the breathing apparatus to perform the various steps of the method.

In a first step, S1, at least one parameter indicative of a degree of $CO_2$ elimination ($VCO_2$) of a mechanically ventilated subject is monitored. As described above, this is preferably performed by monitoring a flow or volume of expiration gas exhaled by the subject, and one or more parameters indicative of the presence of $CO_2$ in said expiration gas, such as the $PACO_2$, the $CO_2$ concentration or the volume of $CO_2$ in said expiration gas. Preferably, said at least one parameter is monitored by means of a capnograph and most preferably by means of a volumetric capnograph capable of deriving the $VCO_2$ of the subject from measured expiration flow and expired $PACO_2$. Said at least one parameter is first monitored during a first phase of ventilation in which the subject is ventilated using a baseline PEEP resulting in a baseline level of $VCO_2$, as illustrated in FIG. 4 in which the $VCO_2$ level during this first phase of ventilation is indicated by reference numeral (A).

In a second step, S2, a sudden change in PEEP is applied to the subject. The change in PEEP defines the transition from the first phase of ventilation to a second phase of ventilation during which the PEEP is maintained at a new (changed) level of PEEP. The at least one parameter indicative of a degree of $VCO_2$ of the subject is monitored also during this second phase of ventilation. The sudden change in PEEP induces a change in $VCO_2$ of the subject by causing a rapid fluctuation in $VCO_2$ (indicated by reference numeral (B) in FIG. 4) before the $VCO_2$ level stabilizes at a new steady state level (indicated by reference numeral (C) in FIG. 4). This second phase of ventilation with a changed PEEP level should last at least until said new steady state (equilibrium) of $VCO_2$ is reached. Typically, the second phase of ventilation of changed PEEP should last for at least 30 seconds and preferably about one minute. Preferably, the change in PEEP is an increase, e.g. a stepwise increase or incremental increase of 5 or 10 $cmH_2O$. However, it is contemplated that also a sudden decrease in PEEP can be used in a similar way to predict the fluid responsiveness of the subject in accordance with the proposed principles.

In a third step, S3, the fluid responsiveness of the subject is predicted based on a change in the at least one monitored parameter indicative of the degree of $VCO_2$, following the change in PEEP in step S2, and typically based on a comparison between values of the at least one monitored parameter prior to and after said change in PEEP. As described above, the subject may be judged to be a responder if the PEEP-induced difference in $CO_2$ elimination ($\Delta VCO_2$) between the baseline level of $VCO_2$ during baseline PEEP ventilation (i.e. during the first phase of ventilation) and the new steady state level of $VCO_2$ during changed PEEP ventilation (i.e. during the second phase of ventilation) exceeds a certain threshold value which, according to one embodiment, may correspond to 10 or even 11% of the baseline $VCO_2$ level.

As indicated in FIG. 4, once the $VCO_2$ level has reached its new steady state level during the second phase of ventilation, the change in PEEP may be removed again. Thus, the step S3 is preferably followed by a step in which the change in PEEP is removed such that PEEP returns to its baseline level, i.e. the level of PEEP prior to the change. The removal of the change in PEEP defines the transition from the second phase of ventilation to a third phase of ventilation in which the $VCO_2$ of the subject is allowed to return to the baseline level of $VCO_2$ (indicated by reference numeral (D) in FIG. 4). Thus, the proposed method for prediction of fluid responsiveness based on PEEP-induced or post-PEEP adjustment changes in $CO_2$ elimination is a fully reversible method which may be frequently repeated without affecting the hemodynamics or the volume status of the patient.

As mentioned above, the method is preferably preceded by a preconditioning maneuver to re-expand collapsed airways and easy re-expandable lung regions. Thus, according to one embodiment, the first step S1 is preceded by a step of providing a sequence of breaths of increased pressure and preferably also increased PEEP to the subject in order to minimize any significant lung re-expansion effect potentially caused by the subsequent PEEP challenge. After said preconditioning maneuver, the change in PEEP in step S2 can be performed when the $VCO_2$ of the subject has assumed a steady state.

Thus, according to the principles of the present disclosure, the fluid responsiveness of a ventilated subject is predicted based on a change in at least one monitored parameter indicative of the $VCO_2$ of the subject, caused by a change in PEEP. In the embodiment described above, the ventilated subject is deemed to be either fluid responsive or non-fluid responsive depending on whether or not the change in the monitored parameter exceeds a predetermined threshold value. In this exemplary embodiment the prediction is thus a binary prediction according to which the subject is deemed to be either responsive or non-responsive to administration of intravascular fluid. The breathing apparatus 1 illustrated in FIG. 2 may be configured to communicate the result of the prediction to an operator of the apparatus, e.g. by displaying an indicator indicating whether the ventilated subject is deemed to be a responder or non-responder on the display 25.

In other embodiments, the prediction may involve determination of a multiple level (more than two) fluid responsiveness index indicative of the likelihood that the subject is responsive to administration of intravascular fluid. This fluid responsiveness index may be determined based on the magnitude of the change in the at least one monitored parameter. For example, the magnitude of the change in the monitored parameter may be compared to reference values in a look-up table stored in the memore 29 of the breathing apparatus 1 (see FIG. 2), whereby the breathing apparatus 1 may be configured to determine a fluid responsiveness index for the subject based on said comparison, and to display the fluid responsiveness index on the display 25. The fluid responsiveness index may, for example, be a value on a scale between 1-5 or 1-10, where a high value indicates that the ventilated subject is deemed likely to respond to administration of intravascular fluid.

Determination of Change in Cardiac Output or EPBF

Often, changes in carbon dioxide elimination ($VCO_2$ [ml/min]) are assumed to be proportional to changes in cardiac output (CO [l/min]). However, changes in carbon dioxide elimination are proportional to changes in cardiac output only if the carbon dioxide level in the lungs of the subject and the lung volume of the subject are constant between the analyzed breaths. If so, the $CO_2$ content in the lungs of the subject is kept constant as the amount of $CO_2$ added to the lungs by the pulmonary blood flow equals the amount of $CO_2$ eliminated through ventilation. Furthermore, changes in carbon dioxide elimination are proportional to the changes in cardiac output only if the shunt fraction and the $CO_2$ content in venous blood are constant between the analyzed breaths.

When a PEEP maneuver is performed, a transient change in effective lung volume of the ventilated subject will occur. After said transient change a substantially steady state appears, which steady state lasts for a time period of approximately one minute. According to the principles of the present disclosure, the relationship between the $CO_2$ elimination of the subject prior to the PEEP maneuver and the $CO_2$ elimination of the subject during said steady state is analyzed to predict the fluid responsiveness of the subject.

In one embodiment, the proposed method for prediction of fluid responsiveness may be implemented to assume a constant level of $CO_2$ in the lungs of the subject between the analyzed breaths. If this assumption is correct, and if the shunt fraction and the $CO_2$ content in venous blood of subject are substantially constant during the analyzed sequence of breaths, the relationship between the different levels of $CO_2$ elimination is a reliable measure of the fluid responsiveness of the subject.

However, the PEEP maneuver changes the pulmonary blood flow of the subject, causing a gradual change in the $CO_2$ level in the lungs of the subject before assuming a new and substantially steady state. Further, the PEEP-induced change in effective lung volume of the subject is sometimes very quick (new steady state assumed after only a few breaths) and sometimes very slow (new steady state assumed after more than ten breaths). Recent studies have shown that the combined effect of these phenomenon is not easy to foresee and that the assumption of constant $CO_2$ level in the lungs of the subject during the period following the PEEP maneuver is often incorrect.

Therefore, in a preferred embodiment, the proposed method for prediction of fluid responsiveness of a ventilated subject is implemented in a manner taking possible variations in the level of $CO_2$ in the lungs of the subject into account, either by measuring and using them in the calculation of fluid responsiveness and/or by actively preventing them. To this end, as will be discussed in more detail below, the proposed method may comprise a step of measuring variations in the level of expired $CO_2$, indicative of variations in the level of $CO_2$ in the lungs of the subject, and using said measurements in the prediction of the fluid responsiveness of the subject, and/or a step of adjusting the ventilation of the subject, e.g. by adjusting the duration of the ventilator respiratory cycles and/or the tidal volume of the breaths delivered by the ventilator, to keep the level of $CO_2$ in the lungs of the subject substantially constant between the analyzed breaths, i.e. between the breaths during which the parameters used for the calculation is measured. The latter may be achieved by automatic feedback control of the ventilator using the measurements of expired $CO_2$ as control parameter.

Below, some equations describing the $CO_2$ dynamics of a single-compartment lung model and how they can be used to analyze the way a PEEP maneuver affects the perfusion of a mechanically ventilated patient will be discussed.

The capnodynamic equation of the lung model (assuming constant ELV and $\Delta t$) can be written as:

$$ELV \cdot (F_A CO2^{-1}) = \Delta t \cdot EPBF^n \cdot (C_v CO2 - C_A CO2^n) - VTCO2^n \quad (\text{eq. 1})$$

In this equation, ELV is the end-expiratory lung volume containing CO2, FACO2 is the fraction of alveolar CO2, EPBF is the effective pulmonary blood flow, CvCO2 is the CO2-content of venous blood, CACO2 is the $CO_2$-content of pulmonary capillary blood having participated in the alveolar gas exchange and $VTCO_2$ is the tidal elimination of $CO_2$.

At equilibrium (steady state), before the PEEP maneuver (superscript 0), we have the following relationship:

$$0 = \Delta t \cdot EPBF^0 \cdot (C_v CO2 - C_A CO2^0) - VTCO2^0 \quad (\text{eq. 2})$$

By introducing a coefficient ($S_{CO2}$) of $CO_2$ solubility in blood in order to express the $CO_2$-content in blood (CxCO2) as fraction of $CO_2$, equations 1 and 2 can be re-written to express EPBF in terms of carbon dioxide elimination, VCO2, and FACO2:

$$EPBF^n = \frac{VTCO2^n + ELV \cdot (F_A CO2^n - F_A CO2^{n-1})}{\Delta t \cdot P_{bar} \cdot S_{CO2} \cdot (F_v CO2 - F_A CO2^n)} \quad (\text{eq. 3})$$

$$EPBF^0 = \frac{VTCO2^0}{\Delta t \cdot P_{bar} \cdot S_{CO2} \cdot (F_v CO2 - F_A CO2^0)} \quad (\text{eq. 4})$$

By forming the quotient of equations 3 and 4, the following relationship is obtained:

$$\frac{EPBF^n}{EPBF^0} = \frac{VTCO2^n + ELV \cdot (F_A CO2^n - F_A CO2^{n-1})}{VCO2^0} \cdot$$
$$\frac{F_v CO2 - F_A CO2^0}{F_v CO2 - F_A CO2^0 + F_A CO2^0 - F_A CO2^n}$$
$$= \frac{VTCO2^n + ELV \cdot (F_A CO2^n - F_A CO2^{n-1})}{VCO2^0} \cdot$$
$$\frac{1}{1 - \frac{F_A CO2^n - F_A CO2^0}{F_v CO2 - F_A CO2^0}} \quad (\text{eq. 5})$$

Starting from equation 5 and assuming constant $CO_2$ level in the lungs of the subject during the analyzed sequence of breaths, we end-up with the relationship (assuming constant duration $\Delta t$ of the respiratory cycles)

$$\frac{EPBF^n}{EPBF^0} = \frac{VTCO2^n}{VTCO2^0} = \frac{VCO2^n / \Delta t}{VCO2^0 / \Delta t} = \frac{VCO2^n}{VCO2^0}, \quad (\text{eq. 6})$$

which relationship may be used to assess the fluid responsiveness of the subject according to some embodiments of the present disclosure. However, if the level of $CO_2$ in the lungs of the subject varies between the analyzed breaths, meaning that the term $F_A CO2^n - F_A CO2^{n-1}$ and/or the term $F_A CO2^n - F_A CO2^0$ is non-zero, equation 6 does not correctly reflect the rather complex relationship expressed by equation 5.

Furthermore, as discussed above, the assumption that ELV is constant between the analyzed breaths is not always correct. If ELV differs between breaths, the capnodynamic equation of the lung model reads:

$$(ELV^n \cdot F_A CO2 - ELV^{n-1} \cdot F_A CO2^{n-1}) = \Delta t \cdot EPBF^n \cdot (C_v CO2 - C_A CO2^n) - VTCO2^n \quad (eq.7)$$

which, by considering that $ELV^n = ELV^{n-1} + \Delta ELV^n$, where $\Delta ELV^n$ is the inspired tidal volume minus the expired tidal volume for breath n ($VTi^n - VTe^n$), may be expressed as:

$$ELV^n (F_A CO2^n - F_A CO2^{n-1}) = \Delta t \cdot EPBF^n \cdot (C_v CO2 - C_A CO2^n) - VTCO2^n - \Delta ELV^n \cdot F_A CO2^{n-1} \quad (eq. 8)$$

Starting out from equation 8, the EPBF quotient may be expressed as:

$$\frac{EPBF^n}{EPBF^0} = \frac{VTCO2^n + \Delta ELV^n \cdot F_A CO2^{n-1}}{VCO2^0} \cdot \underbrace{\left(1 + \frac{ELV^n \cdot (F_A CO2^n - F_A CO2^{n-1})}{VCO2^0}\right)}_{A} \cdot \underbrace{\frac{1}{1 - \frac{F_A CO2^n - F_A CO2^0}{F_v CO2 - F_A CO2^0}}}_{B} \quad (eq. 9)$$

By studying equation 9, it can be realized that if FACO2 is constant between the analyzed breaths ($FACO2^0 = FACO2^{n-1} = FACO2^n$), meaning that the level of $CO_2$ in the lungs of the patient is kept constant, the factors A and B are eliminated and equation 9 differs from equation 6 only by the readily measurable term $\Delta ELV^n \cdot FACO2^{n-1}$ which is added to the numerator of the quotient $VTCO2^n / VTCO2^0$. If, however, FACO2 is not constant between the analyzed breaths, the remaining factors A and B need to be dealt with somehow.

The above discussions relate to the EPBF of the ventilated subject. To see how the cardiac output (CO) of the subject is affected by the PEEP-maneuver we introduce the shunt fraction, $f_s$, relating EPBF to cardiac output according to the formula:

$$CO \cdot (1 - f_s) = EPBF \quad (eq. 10)$$

Introducing this relationship in equation 9 yields:

$$\frac{CO^n}{CO^0} = \frac{VTCO2^n + \Delta ELV^n \cdot F_A CO2^{n-1}}{VCO2^0} \cdot \frac{1 - f_s^0}{1 - f_s^n} \cdot \underbrace{\left(1 + \frac{ELV^n \cdot (F_A CO2^n - F_A CO2^{n-1})}{VCO2^0}\right)}_{A} \cdot \underbrace{\frac{1}{1 - \frac{F_A CO2^n - F_A CO2^0}{F_v CO2 - F_A CO2^0}}}_{B} \quad (e. 11)$$

Clearly, if the shunt fraction varies during the analyzed sequence of breaths, the PEEP-induced change in cardiac output and so the fluid responsiveness of the subject becomes more difficult to quantify.

Taking the above algorithms into consideration, it becomes clear that the change in carbon dioxide elimination caused by the PEEP maneuver is not necessarily a true indicator of the change in cardiac output of the subject. Variations in the shunt fraction of the subject, variations in the $CO_2$ level in the lungs of the subject and variations in the effective lung volume of the subject between the analyzed breaths need also to be taken into account in order to more accurately quantify the change in cardiac output.

To minimize variations in shunt fraction of the ventilated subject following the PEEP maneuver, the method for prediction of fluid responsiveness may involve a step of applying a preconditioning maneuver to the subject prior to applying the PEEP maneuver, which preconditioning maneuver serves to minimize the risk of variations in the shunt fraction, fs, and any significant lung re-expansion effect following the PEEP maneuver. The preconditioning maneuver involves delivery of a sequence of high-pressure breaths, i.e. a sequence of breaths of increased pressure compared to baseline ventilation. Preferably said sequence of breaths is delivered at increased PEEP, i.e. at a PEEP level that is increased compared to the PEEP level at baseline ventilation.

Furthermore, the method may involve the step of determining the directly measurable parameters FACO2, VTCO2 and $\Delta ELV$. Preferably but not necessarily, these parameters are measured for each breath in the sequence of breaths 0 to n, i.e. for each breath between a first point in time occurring at or prior to application of the PEEP maneuver (breath number 0) and a second point in time occurring after the PEEP maneuver when the carbon dioxide elimination has reached a new and substantially steady state (breath number n), typically about one minute after application of the PEEP maneuver.

The carbon dioxide elimination of the subject (VCO2) may be determined from the expiratory flow and the $CO_2$ content of expiration gases exhaled by the subject, and the tidal $CO_2$ elimination (VTCO2) may be determined from VCO2 and the duration of the respiratory cycle ($\Delta t$). $\Delta ELV$ may be determined from the inspiratory and expiratory tidal volumes of the subject. FACO2 may also be determined from the expiratory flow and the $CO_2$ content of expiration gases exhaled by the subject. For example, FACO2 may be determined from a capnogram captured by a volumetric capnograph measuring expiration flow or volume and the fraction (or partial pressure) of $CO_2$ in the expiration gases. FACO2 may be estimated as the end-tidal fraction of expired $CO_2$ (FetCO2) given by the volumetric capnogram but is preferably estimated as a $CO_2$ value found at or near the midpoint of the alveolar slope (phase III) of the volumetric capnogram, which $CO_2$ value has been found to best represent the alveolar fraction or partial pressure of $CO_2$.

As regards possible variations in the level of $CO_2$ in the lungs of the subject (manifested as variations in measured FACO2) between the analyzed breaths, such variations can be dealt with in any or both of the following ways:

1) They can be used in the determination of the fluid responsiveness of the subject by using measured FACO2 values in the calculation of the PEEP-induced change in cardiac output or EPBF, e.g. as calculated in accordance with equation 9 or 11 using determined FACO2 values for breaths 0, n−1 and n. However, this approach requires ELV and $F_v CO2$ to be estimated, undesirably increasing the uncertainty in the determination of the change in cardiac output. ELV and $F_v CO2$ may be estimated in several different ways known by the person skilled in the art. For example, ELV and $F_vCO2$ may be estimated using the method disclosed in WO WO2013/141766 A1, which method allows both ELV and $F_vCO2$ (after conversion of $C_vCO2$ to $F_vCO2$ using the coefficient of $CO_2$ solubility in blood, $S_{CO2}$) to be simultaneously and non-invasively determined through three-dimensional correlation analysis.

2) They can be prevented by actively controlling the ventilator to keep the $CO_2$ level in the lungs of the subject substantially constant between the analyzed breaths. This may be achieved by controlling the ventilator to keep the measured FACO2 level substantially constant between breaths, i.e. to keep the FACO2 level after application of the PEEP maneuver substantially equal to the FACO2 level prior to the PEEP maneuver (i.e. substantially equal to $FACO2^0$. To this end, the control processor of the ventilator may be configured to adjust the ventilation of the patient based on the measured FACO2 values, preferably measured on a breath-by-breath basis. By keeping the FACO2 level substantially constant between the analyzed breaths, the factors A and B in equations 9 and 11 can be ignored, and the change in EPBF or cardiac output can be reliably determined by the control processor from the measured VTCO2, $\Delta$ELV and FACO2 values. In more detail, the change in EPBF or cardiac output can be determined from $VTCO2^0$, $VTCO2^n$, $\Delta ELV^n$ and $FACO2^{n-1}$ (or the FACO2 value obtained for any breath in the sequence of breaths 0 to n since FACO2 is kept constant during said sequence of breaths). Although, with this approach, VTCO2 needs to be determined only for breath 0 and n, the carbon dioxide elimination of the subject is preferably measured for each breath in the sequence of breaths 0 to n in order to determine when a new steady state level has been reached following the change in PEEP. Likewise, FACO2 is preferably measured for each breath in the sequence of breaths 0 to n and used as control parameter in order for the control processor to adjust the ventilation to keep FACO2 substantially constant between breaths. The measured FACO2 values may also be used to verify that FACO2 has indeed remained substantially constant between the analyzed breaths. If, in spite of active control of the ventilator to keep FACO2 constant, it is found that FACO2 varies too much (e.g. more than a certain threshold value), the ventilator may be configured to use the varying FACO2 values in the calculation of the change in cardiac output or EPBF, as described above.

The second option of preventing variations in the level of $CO_2$ in the lungs of the subject through automatic control of the ventilation provided to the subject by the ventilator may, in one exemplary embodiment, involve control of the tidal volume ($VT^n$) of the breaths delivered by the ventilator. By adjusting the tidal volume on a breath-by-breath basis based on the FACO2 value measured during one or more preceding breaths, the tidal volume can be varied to keep FACO2 substantially constant. However, changes in delivered tidal volume may undesirably affect the lung dynamics of the ventilated subject, e.g. by re-opening closed alveoli. Therefore, according to a preferred embodiment, variations in the level of $CO_2$ in the lungs of the subject may instead be prevented by controlling the duration of the respiratory cycles provided by the ventilator, i.e. by adjusting the duration of the breaths delivered by the ventilator. Preferably, the duration of the respiratory cycle is adjusted by adjusting the pause between the end of expiration of a preceding breath and the start of inspiration of the following breath (i.e. by adjusting the "expiratory pause"). If the level of $CO_2$ in the lungs of the subject, as manifested by measured FACO2 values, starts to decrease, the expiratory pause may be prolonged, and if the level of $CO_2$ in the lungs of the subject starts to increase, the expiratory pause may be shortened. If equation 11 is modified to account for variations in the duration ($\Delta t^n$) of the respective breath in the analyzed sequence of breaths, the quotient $CO^n/CO^0$ is given by the following equation:

$$\frac{CO^n}{CO^0} = \frac{\Delta t^0}{\Delta t^n} \cdot \frac{VTCO2^n + \Delta ELV^n \cdot F_A CO2^{n-1}}{VTCO2^0} \cdot \qquad (eq.\ 12)$$

$$\underbrace{\frac{1-f_s^0}{1-f_s^n} \cdot \left(1 + \frac{ELV^n \cdot (F_A CO2^n - F_A CO2^{n-1})}{VCO2^0}\right)}_{A} \cdot$$

$$\underbrace{\frac{1}{1 - \frac{F_A CO2^n - F_A CO2^0}{F_v CO2 - F_A CO2^0}}}_{B}$$

Assuming constant shunt fraction ($f_s$), the factor $(1-f_s^0/(1-f_s^n)$ in eq. 12 is eliminated and the quotients $CO^n/CO^0$ and $EPBF^n/EPBF^0$ are given by:

$$\frac{CO^n}{CO^0} = \frac{EPBF^n}{EPBF^0} = \frac{\Delta t^0}{\Delta t^n} \cdot \frac{VTCO2^n + \Delta ELV^n \cdot F_A CO2^{n-1}}{VTCO2^0} \cdot \cdot \qquad (eq.\ 13)$$

$$\underbrace{\left(1 + \frac{ELV^n \cdot (F_A CO2^n - F_A CO2^{n-1})}{VCO2^0}\right)}_{A} \cdot$$

$$\underbrace{\frac{1}{1 - \frac{F_A CO2^n - F_A CO2^0}{F_v CO2 - F_A CO2^0}}}_{B}$$

By adjusting $\Delta t$, e.g. on a breath-by-breath basis, to keep $FACO_2$ substantially constant and equal to $FACO_2^0$ during the sequence of breaths 0 to n, the factors A and B are eliminated and the quotients $CO^n/CO^0$ and $EPBF^n/EPBF^0$ are given by:

$$\frac{CO^n}{CO^0} = \frac{EPBF^n}{EPBF^0} = \frac{\Delta t^0}{\Delta t^n} \cdot \frac{VTCO2^n + \Delta ELV^n \cdot F_A CO2^{n-1}}{VTCO2^0}, \qquad (eq.\ 14)$$

where $FACO2^{n-1}$ can be substituted for $FACO2^x$ as FACO2 is kept substantially constant between breaths.

Thus, the quotients $CO^n/CO^0$ and $EPBF^n/EPBF^0$ indicative of the change in cardiac output and EPBF of the ventilated subject caused by the applied PEEP maneuver, and so indicative of the fluid responsiveness of the subject, may be determined from measured VTCO2, $\Delta$ELV and FACO2 values alone if FACO2 is kept substantially constant between the analyzed breaths (i.e. breaths number 0, n−1 and n). If, however, FACO2 is not or cannot be kept constant between the analyzed breaths, e.g. through automatic adjustment of the duration ($\Delta t$) of delivered breaths, the effective lung volume of the subject and/or the venous $CO_2$ of the subject should preferably be estimated and used in combination with VTCO2, $\Delta$ELV and FACO2 in the determination of the $CO^n/CO^0$ or $EPBF^n/EPBF^0$ quotient, in accordance with equation 13.

Above, the calculation of the change in cardiac output or EPBF has been described in the context of the foregoing description related to determination of fluid responsiveness of a ventilated subject, however, it should be realized that the rationale behind the calculations is not limited to the assessment of fluid responsiveness of the subject. The magnitude of the change in cardiac output or EPBF in response to any challenge potentially changing the cardiac output or EPBF of the subject may be a useful parameter also in the assessment of other physiological states of the ventilated subject. Therefore, it should be understood that the method for determination of changes in cardiac output or EPBF of a ventilated subject described above may be advantageously used also for other purposes than the assessment of fluid responsiveness.

In the foregoing description, the change in cardiac output is effectuated by a PEEP maneuver causing a change in the $CO_2$ elimination of the subject. However, the above discussion on determination of changes in cardiac output or EPBF is not limited to any particular maneuver or challenge, and any maneuver or challenge potentially causing a change in the cardiac output and/or EPBF of the subject may be used. A challenge or maneuver potentially causing a change in the cardiac output and/or the EPBF of a ventilated subject will hereinafter be referred to as a cardiac output challenge. Non-exclusive examples of cardiac output challenges are PEEP maneuvers, fluid challenges and passive leg raising maneuvers.

Furthermore, the above calculations rely on the fraction of alveolar $CO_2$ (FACO2) as indicator of any change in the level of $CO_2$ in the lungs of the subject. However, any parameter indicative of the level of $CO_2$ in the lungs of the subject may be used instead of FACO2. For example, FACO2 may be substituted for a measured value of the fraction or partial pressure of expired $CO_2$ (FECO2 or PECO2), e.g. the end-tidal fraction or partial pressure of expired $CO_2$ (FetCO2 or PetCO2).

Consequently, according to one aspect of the present disclosure, there is provided a method for determining a change in cardiac output or effective pulmonary blood flow (EPBF) of a subject connected to a breathing apparatus, such as a ventilator, comprising the steps of:
  applying a cardiac output challenge to the subject;
  determining a first level of carbon dioxide elimination of the subject at a first point in time occurring at or prior to application of said cardiac output challenge;
  determining a second level of carbon dioxide elimination of the subject at a second point in time occurring after application of said cardiac output challenge, and
  calculating a change in cardiac output or effective pulmonary blood flow (EPBF) of the subject based on said first and second levels of carbon dioxide elimination;
  determining a parameter indicative of the level of $CO_2$ in the lungs of the subject, and
  using said parameter in the calculation of the change in cardiac output or effective pulmonary blood flow.

Said parameter may be FACO2, PACO2 or any surrogate measure of alveolar $CO_2$ of the subject, such as FetCO2 or PetCO2, or any other parameter indicative of the of the level of $CO_2$ in the lungs of the subject.

As clear from above, the method typically involves the step of taking possible variations in said parameter into account during determination of the change in cardiac output or EPBF. Possible variations may be taken into account by measuring and using them in the calculation of cardiac output or EPBF and/or by actively preventing them by adjusting the ventilation provided by the breathing apparatus to keep the parameter substantially constant, at least between analyzed breaths and preferably between said first and second points of time.

Measuring and using variations in said parameter typically means that the parameter is determined repeatedly, preferably on a breath-by-breath basis, and that at least some of the varying parameter values are used to calculate the change in cardiac output or EPBF, e.g. based on the relations expressed by equation 13.

Actively preventing them by adjusting the ventilation provided by the breathing apparatus typically means that the tidal volume and/or the duration of the breaths delivered by the breathing apparatus is adjusted to keep the parameter substantially constant, at least between the analyzed breaths and preferably between said first and second points of time. In this case, as discussed above, the change in cardiac output or EPBF may be calculated based on the relations expressed by equation 14.

The step of adjusting the ventilation provided by the breathing apparatus to keep the parameter substantially constant typically involves adjusting the tidal volume and/or the duration of the breaths delivered by the breathing apparatus.

Determination of the parameter indicative of the level of carbon dioxide in the lungs of the subject is preferably performed repeatedly, e.g. on a breath-by-breath basis. The repeatedly determined parameter values may be used as control parameter by the control processor of the breathing apparatus in order to automatically adjust the ventilation of the subject to keep the parameter substantially constant.

Furthermore, the repeatedly determined parameter values may be used to determine if the parameter is substantially constant or if the parameter varies between breaths. If the parameter is substantially constant, the change in cardiac output or EPBF may be calculated according to a first principle and, if the parameter varies, the change in cardiac output or EPBF may be calculated according to a second and different principle. The first principle may involve calculation of the change in cardiac output or EPBF based on the relations expressed by equation 14 and the second principle may involve calculation of the change in cardiac output or EPBF based on the relations expressed by equation 13. The control processor of the breathing apparatus may be configured to calculate the change in cardiac output or EPBF according to the first or the second principle in dependence of whether the repeatedly determined parameter is substantially constant or not.

As discussed in the foregoing, the calculated change in cardiac output or EPBF may be used to assess the fluid responsiveness of the ventilated subject but may also be used in the assessment of other physiological states of the subject.

As also discussed in the foregoing, the cardiac output challenge may be a PEEP maneuver but may also be any other type of challenge potentially changing the cardiac output or the EPBF of the subject, such as a fluid challenge or passive leg raising maneuver.

Figure 1:
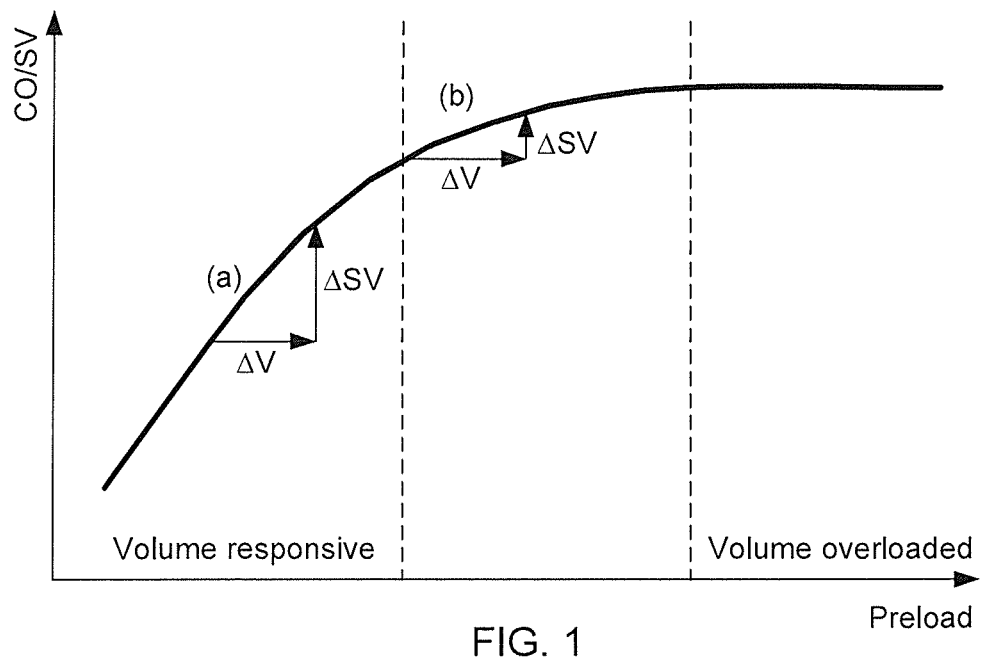
FIG. 1 illustrates the Frank-Starling curve as the increase in cardiac output or stroke volume in response to changes in preload obtained by the administration of an intravascular volume of liquid.

It should be appreciated that the method for determining a change in cardiac output or EPBF of the ventilated subject is typically performed by the control processor 27 of the breathing apparatus 1 illustrated in FIG. 1, when the subject is connected to and ventilated by said breathing apparatus.

Thus, according to another aspect of the present disclosure there is provided a breathing apparatus 1, such as a ventilator, for determining a change in cardiac output or effective pulmonary blood flow of a subject 3 connected to the breathing apparatus 1. The breathing apparatus 1 has a control processor 27 configured to:
- determine a first level of carbon dioxide elimination of the subject at a first point in time occurring at or prior to the application of a cardiac output challenge to the subject 3;
- determine a second level of carbon dioxide elimination of the subject at a second point in time occurring after application of said cardiac output challenge, and
- calculate a change in cardiac output or effective pulmonary blood flow of the subject 3 based on said first and second levels of carbon dioxide elimination;
- determine a parameter indicative of the level of carbon dioxide in the lungs of the subject 3, and
- use said parameter in the calculation of the change in cardiac output or effective pulmonary blood flow (EPBF).

The control processor 27 may further be configured to perform any of or any combination of the above described method steps relating to the method for determination of a change in cardiac output or EPBF of a subject connected to the breathing apparatus 1.

The control processor 27 is typically configured to carry out the method steps through execution of a computer program, which computer program may be stored in a non-volatile memore 29 of the breathing apparatus 1. Thus, according to yet another aspect of the present invention, a non-transitory, computer-readable data storage medium encoded with programming instructions for determining a change in cardiac output or effective pulmonary blood flow of a subject 3 connected to a breathing apparatus 1. The programming instructions are in computer-readable code that, when executed by a processor 21 of the breathing apparatus 1, causes the breathing apparatus 1 to:
- determine a first level of carbon dioxide elimination of the subject at a first point in time occurring at or prior to application of a cardiac output challenge to the subject 3;
- determine a second level of carbon dioxide elimination of the subject at a second point in time occurring after application of said cardiac output challenge, and
- calculate a change in cardiac output or effective pulmonary blood flow (EPBF) of the subject based on said first and second levels of carbon dioxide elimination;
- determine a parameter indicative of the level of $CO_2$ in the lungs of the subject, and
- use said parameter in the calculation of the change in cardiac output or effective pulmonary blood flow.

The computer program may further have code that, when executed by said processor 21, causes the breathing apparatus 1 to perform any of or any combination of the above described method steps relating to the method for determination of a change in cardiac output or EPBF of a subject connected to the is breathing apparatus 1.

Previously in the present disclosure there has been presented a method for prediction of fluid responsiveness of a subject 3 connected to the breathing apparatus 1 capable of providing mechanical ventilation to said subject 3, including the steps of:
- monitoring at least one parameter indicative of a degree of carbon dioxide elimination of the subject;
- applying a PEEP maneuver in which a PEEP applied to the subject is changed from a first PEEP level to a second PEEP level, and
- predicting the fluid responsiveness of the subject based on a change in said at least one monitored parameter following said change in PEEP.

In accordance with the above discussed findings that the change in carbon dioxide elimination is not always a very precise measure of changes in cardiac output and EPBF of the subject, the prediction of fluid responsiveness is preferably based also on a parameter indicative of the level of carbon dioxide in the lungs of the subject. To this end, the method for prediction of fluid responsiveness may include the additional steps of:
- determining a parameter indicative of the level of carbon dioxide in the lungs of the subject;
- calculating a change in cardiac output or EPBF based on both said change in the at least one monitored parameter indicative of a degree of carbon dioxide elimination of the subject following said change in PEEP and said parameter indicative of the level of carbon dioxide in the lungs of the subject, and
- predicting the fluid responsiveness of the subject 3 based on the calculated change in cardiac output or EPBF.

Furthermore, the method for prediction of fluid responsiveness may include any of or any combination of the above described method steps relating to the method for determination of a change in cardiac output or EPBF of a subject in order to more accurately determine the change in cardiac output or EPBF and so more accurately predict the fluid responsiveness of the subject. For example, it may comprise the step of taking possible variations in said parameter indicative of the level of carbon dioxide in the lungs of the subject into account during determination of the change in cardiac output or EPBF, e.g. by measuring them and using them in the calculation of cardiac output or EPBF and/or by actively preventing them by adjusting the ventilation provided by the breathing apparatus 1 to keep said parameter substantially constant. Here too, the calculated change in cardiac output or EPBF is preferably calculated based on the relations expressed in either equation 13 or equation 14, depending on whether or not the parameter indicative of the level of carbon dioxide in the lungs of the subject varies between breaths.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for prediction of fluid responsiveness of a subject connected to a breathing apparatus that is operable to provide mechanical ventilation to said subject, said method comprising:
- in a processor, monitoring at least one parameter indicative of a degree of carbon dioxide elimination of the subject;
- from said processor, controlling a positive end expiratory pressure (PEEP) regulator of the breathing apparatus to apply a PEEP maneuver to the subject in which a PEEP applied to the subject is changed from a first PEEP level to a second PEEP level; and
- in said processor, predicting a fluid responsiveness of the subject based on a change in said at least one monitored parameter following said change in PEEP, and making an electronic signal representing the predicted fluid responsiveness available as an output from said processor; and
- before changing the PEEP level in order to determine the change in said at least one monitored parameter, operating said breathing apparatus from said processor to execute a preconditioning maneuver in which a sequence of breaths of increased pressure is provided to the subject.

2. Method according to claim 1, comprising determining the change in said at least one monitored parameter as a difference between a substantially steady state level of said parameter prior to said change in PEEP, and a new substantially steady state level of said parameter after said change in PEEP.

3. Method according to claim 1, comprising determining the change in said at least one monitored parameter is determined based on a difference between at least one pre-PEEP adjustment value of said at least one monitored parameter obtained prior to said change in PEEP, and at least one post-PEEP adjustment value of said at least one monitored parameter obtained after said change in PEEP, and obtaining said at least one post-PEEP adjustment value of the monitored parameter in a range of 10-120 seconds after said change in PEEP.

4. Method according to claim 1, comprising making said electronic signal representing the predicted fluid responsiveness available as an output from said processor by visually and/or audibly signaling to an operator of the breathing apparatus whether the subject is fluid responsive or not fluid responsive based on said prediction.

5. Method according to claim 1, comprising predicting said fluid responsiveness by determining a degree of fluid responsiveness of said subject based on the change in said at least one monitored parameter following said change in PEEP, or based on the change in PEEP required to make the change in magnitude of said at least one monitored parameter exceed a predetermined threshold value, and wherein making said electronic signal representing the predicted fluid responsiveness available as an output from said processor comprises visually and/or audibly communicating said degree of fluid responsiveness to an operator of the breathing apparatus.

6. A method as claimed in claim 1 comprising, in said processor, monitoring a volume or flow of carbon dioxide elimination per breath by the subject ($VCO_2$), as said at least one parameter indicative of the degree of carbon dioxide elimination.

7. Method according to claim 6, comprising making the prediction based on a change in the carbon dioxide elimination ($\Delta VCO_2$) of the subject following said change in PEEP.

8. Method according to claim 7, wherein predicting said fluid responsiveness comprises determining the subject to be fluid-responsive when said change in $CO_2$ elimination ($\Delta VCO_2$) exceeds a predetermined threshold value.

9. Method according to claim 7, comprising determining the carbon dioxide elimination of the subject based on a measured flow or volume of expiration gas exhaled by said subject, and at least one measured parameter indicative of the presence of $CO_2$ in said expiration gas, such as the concentration, volume or partial pressure of $CO_2$ in said expiration gas.

10. A breathing apparatus for prediction of fluid responsiveness of a subject connected to the breathing apparatus, the breathing apparatus comprising:
 a PEEP regulator configured to regulate a positive end-expiratory pressure, PEEP, applied to said subject;
 a control processor configured to control said PEEP regulator to monitor at least one parameter indicative of a degree of carbon dioxide elimination of the subject; said control processor being configured to control said PEEP regulator to apply a PEEP maneuver in which the PEEP applied to the subject is changed from a first PEEP level to a second PEEP level, to predict a fluid responsiveness of the subject based on a change in said at least one monitored parameter following said change in PEEP, to make an electronic signal representing the predicted fluid responsiveness available as an output from said processor, and before changing the PEEP level in order to determine the change in said at least one monitored parameter, to operate said breathing apparatus to execute a preconditioning maneuver in which a sequence of breathes of increased pressure is provided to the subject.

11. The breathing apparatus according to claim 10, further comprising a sensor configured to measure a flow or volume of expiration gas exhaled by the subject, and a parameter indicative of the presence of carbon dioxide in said expiration gas, selected from the group consisting of partial pressure, concentration, or volume of $CO_2$ in the expiration gas.

12. The breathing apparatus according to claim 11, wherein the control processor is configured to determine the carbon dioxide elimination of the subject based on a measured flow or volume of expiration gas exhaled by said subject, and said at least one measured parameter indicative of the presence of CO2 in said expiration gas.

13. The breathing apparatus according to claim 10, wherein the control processor is configured to determine said change in the monitored parameter as a difference between a substantially steady state level of said parameter prior to said change in PEEP, and a new substantially steady state level of said parameter after said change in PEEP.

14. The breathing apparatus according to claim 10, wherein the control processor is configured to determine the change in said at least one monitored parameter based on a difference between at least one pre-PEEP adjustment value of said at least one monitored parameter obtained prior to said change in PEEP, and at least one post-PEEP adjustment value of said at least one monitored parameter obtained after said change in PEEP, wherein said at least one post-PEEP adjustment value of the monitored parameter is obtained in a range of 10-120 seconds after said change in PEEP.

15. The breathing apparatus according to claim 10, wherein the control processor is configured to operate the breathing apparatus to execute preconditioning maneuver by providing a sequence of breaths of increased pressure to the subject prior to execute changing the PEEP in order to determine the change in said at least one monitored parameter.

16. The breathing apparatus according to claim 10, wherein the control processor is configured to make said electronic signal representing the predicted fluid responsiveness available as an output from said processor by visually and/or audibly signaling to an operator of the breathing apparatus whether the subject is fluid responsive or not fluid responsive based on said prediction.

17. The breathing apparatus according to claim 10, wherein the control processor is configured to determine a degree of fluid responsiveness of said subject based on the change in said at least one monitored parameter following said change in PEEP, or based on the change in PEEP required to make the change in magnitude of said at least one monitored parameter exceed a predetermined threshold value, and to make said electronic signal representing the predicted fluid responsiveness available as an output from said processor by visually and/or audibly communicating said degree of fluid responsiveness to an operator of the breathing apparatus.

18. A breathing apparatus as claimed in claim 10 wherein said control processor is configured to monitor a volume or flow of carbon dioxide elimination per breath by the subject ($VCO_2$), as said at least one parameter indicative of the degree of carbon dioxide elimination.

19. The breathing apparatus according to claim 18, wherein the control processor is configured to predict the fluid responsiveness of the subject based on a change in the carbon dioxide elimination ($\Delta VCO_2$) of the subject following said change in PEEP.

20. The breathing apparatus according to claim 19, wherein the control processor is configured to determine the subject to be fluid-responsive when said change in CO2 elimination ($\Delta VCO_2$) exceeds a predetermined threshold value.

21. A non-transitory, computer-readable data storage medium encoded with programming instructions, said storage medium being loaded into a control computer of a breathing apparatus adapted for connection to a subject, said breathing apparatus comprising a positive end expiratory pressure (PEEP) regulator, said programming instructions causing said control computer to:
monitor at least one parameter indicative of a degree of carbon dioxide elimination of the subject;
control the PEEP regulator to apply a PEEP maneuver to the subject in which a PEEP applied to the subject is changed from a first PEEP level to a second PEEP level; and
predict a fluid responsiveness of the subject based on a change in said at least one monitored parameter following said change in PEEP, and make an electronic signal representing the predicted fluid responsiveness available as an output from said processor; and
before changing the PEEP level in order to determine the change in said at least one monitored parameter, operate said breathing apparatus to execute a preconditioning maneuver in which a sequence of breaths of increased pressure is provided to the subject.

22. A non-transitory, computer-readable data storage medium as claimed in claim 21, wherein said programming instructions cause said control computer to monitor a volume or flow of carbon dioxide eliminated per breath by the subject ($VCO_2$), as said at least one parameter indicative of the degree of carbon dioxide elimination.

23. A method for prediction of fluid responsiveness of a subject connected to a breathing apparatus that is operable to provide mechanical ventilation to said subject, said method comprising:
in a processor, monitoring at least one parameter indicative of a degree of carbon dioxide elimination of the subject;
from said processor, controlling a positive end expiratory pressure (PEEP) regulator of the breathing apparatus to apply a PEEP maneuver to the subject in which a PEEP applied to the subject is changed from a first PEEP level to a second PEEP level; and
in said processor, predicting a fluid responsiveness of the subject based on a change in said at least one monitored parameter indicative of a degree of carbon dioxide elimination following said change in PEEP, and making an electronic signal representing the predicted fluid responsiveness available as an output from said processor;
determining a parameter indicative of the level of carbon dioxide in the lungs of the subject; and
determining a change in cardiac output or effective pulmonary blood flow (EPBF) of the subject based on said change in the at least one monitored parameter indicative of a degree of carbon dioxide elimination;
wherein variations in the parameter indicative of the level of carbon dioxide in the lungs of the subject are taken into account during determination of the change in cardiac output or EPBF by:
measuring the variations and using the variations in a calculation of cardiac output or EPBF, or
adjusting the mechanical ventilation provided by the breathing apparatus to keep said parameter indicative of the level of carbon dioxide in the lungs of the subject substantially constant, and predicting the fluid responsiveness of the subject based on the determined change in cardiac output or EPBF.

24. A breathing apparatus for prediction of fluid responsiveness of a subject and operable to provide mechanical ventilation to said subject, said apparatus comprising:
a processor configured to monitor at least one parameter indicative of a degree of carbon dioxide elimination of the subject;
said processor configured to control a positive end expiratory pressure (PEEP) regulator of the breathing apparatus to apply a PEEP maneuver to the subject in which a PEEP applied to the subject is changed from a first PEEP level to a second PEEP level; and
said processor configured to predict a fluid responsiveness of the subject based on a change in said at least one monitored parameter indicative of a degree of carbon dioxide elimination following said change in PEEP, and make an electronic signal representing the predicted fluid responsiveness available as an output from said processor;
said processor configured to determine a parameter indicative of the level of carbon dioxide in the lungs of the subject; and
said processor configured to determine a change in cardiac output or effective pulmonary blood flow (EPBF) of the subject based on said change in the at least one monitored parameter indicative of a degree of carbon dioxide elimination;
wherein variations in the parameter indicative of the level of carbon dioxide in the lungs of the subject are taken into account during determination of the change in cardiac output or EPBF by:
measuring the variations and using the variations in a calculation of cardiac output or EPBF, or
adjusting the mechanical ventilation provided by the breathing apparatus to keep said parameter indicative of the level of carbon dioxide in the lungs of the subject substantially constant, and predicting the fluid responsiveness of the subject based on the determined change in cardiac output or EPBF.

25. A non-transitory, computer-readable data storage medium encoded with programming instructions, said storage medium being loaded into a control computer of a breathing apparatus operable to predict fluid responsiveness of a subject and to provide mechanical ventilation to said subject, said programming instructions causing said control computer to:
monitor at least one parameter indicative of a degree of carbon dioxide elimination of the subject;
control a positive end expiratory pressure (PEEP) regulator of the breathing apparatus to apply a PEEP maneuver to the subject in which a PEEP applied to the subject is changed from a first PEEP level to a second PEEP level; and predict a fluid responsiveness of the subject based on a change in said at least one monitored parameter indicative of a degree of carbon dioxide elimination following said change in PEEP, and make an electronic signal representing the predicted fluid responsiveness available as an output from said processor;

determine a parameter indicative of the level of carbon dioxide in the lungs of the subject; and determine a change in cardiac output or effective pulmonary blood flow (EPBF) of the subject based on said change in the at least one monitored parameter indicative of a degree of carbon dioxide elimination;

wherein variations in the parameter indicative of the level of carbon dioxide in the lungs of the subject are taken into account during determination of the change in cardiac output or EPBF by:

measuring the variations and using the variations in a calculation of cardiac output or EPBF, or adjusting the mechanical ventilation provided by the breathing apparatus to keep said parameter indicative of the level of carbon dioxide in the lungs of the subject substantially constant, and predicting the fluid responsiveness of the subject based on the determined change in cardiac output or EPBF.

* * * * *